(12) United States Patent
Arts et al.

(10) Patent No.: US 11,105,805 B2
(45) Date of Patent: *Aug. 31, 2021

(54) METHOD FOR DETECTING HIV-1 CO-RECEPTOR TROPISM

(71) Applicant: CASE WESTERN RESERVE UNIVERSITY, Cleveland, OH (US)

(72) Inventors: Eric J. Arts, Ontario (CA); Alison Laing Wright, Cleveland, OH (US); Kevin V. King, Cleveland, OH (US); Miguel E. Quinones-Mateu, Cleveland, OH (US)

(73) Assignee: CASE WESTERN RESERVE UNIVERISTY, Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/411,992

(22) Filed: May 14, 2019

(65) Prior Publication Data

US 2019/0339274 A1 Nov. 7, 2019

Related U.S. Application Data

(63) Continuation of application No. 14/195,528, filed on Mar. 3, 2014, now Pat. No. 10,288,613.

(60) Provisional application No. 61/826,548, filed on May 23, 2013, provisional application No. 61/771,401, filed on Mar. 1, 2013.

(51) Int. Cl.
| | |
|---|---|
| C12N 15/10 | (2006.01) |
| G01N 33/569 | (2006.01) |
| C12Q 1/70 | (2006.01) |
| C12N 15/81 | (2006.01) |
| C12Q 1/686 | (2018.01) |

(52) U.S. Cl.
CPC ...... *G01N 33/56988* (2013.01); *C12N 15/1086* (2013.01); *C12Q 1/703* (2013.01); *C12N 15/81* (2013.01); *C12N 2740/16011* (2013.01); *C12N 2740/16021* (2013.01); *C12N 2740/16022* (2013.01); *C12N 2740/16111* (2013.01); *C12N 2740/16122* (2013.01); *C12Q 1/686* (2013.01)

(58) Field of Classification Search
CPC .............. G01N 33/56988; C12Q 1/703; C12N 15/1086; C12N 2740/16122; C12N 2740/16111; C12N 2740/16021; C12N 2740/16011; C12N 2740/16022
See application file for complete search history.

(56) References Cited

U.S. PATENT DOCUMENTS 10,288,613 B2 * 5/2019 Arts ...................... C12Q 1/703

OTHER PUBLICATIONS

Dudley, D. M., et al., May 2009, A novel yeast-based recombination method to clone and propagate diverse HIV-1 isolates, BioTechniques 46:458-467.*

(Continued)

*Primary Examiner* — Jeffrey S Parkin
(74) *Attorney, Agent, or Firm* — Tarolli, Sundheim, Covell & Tummino LLP

(57) ABSTRACT

A method for determining HIV-1 co-receptor tropism in an HIV-infected patient includes preparing an HIV-1 envelope protein coding sequence from a sample, introducing the HIV-1 envelope protein coding sequence into a first expression construct using yeast homologous recombination, and using the first expression construct in a cell to cell fusion assay to determine HIV-1 co-receptor tropism.

9 Claims, 10 Drawing Sheets

Specification includes a Sequence Listing.

(56) References Cited

OTHER PUBLICATIONS

Holland, A. U., et al., 2004, Alpha-complementation assay for HIV envelope glycoprotein-mediated fusion, 319:343-352.*
Dudley, D. M., et al., 2009, A novel yeast-based recombination method to clone and propagate diverse HIV-1 isolates, Bio Techniques 46(6):458-467.
Holland, A. U., et al., 2004, alpha-Complementation assay for HIV envelope glycoprotein-mediated fusion, Virol. 319:343-352.

* cited by examiner

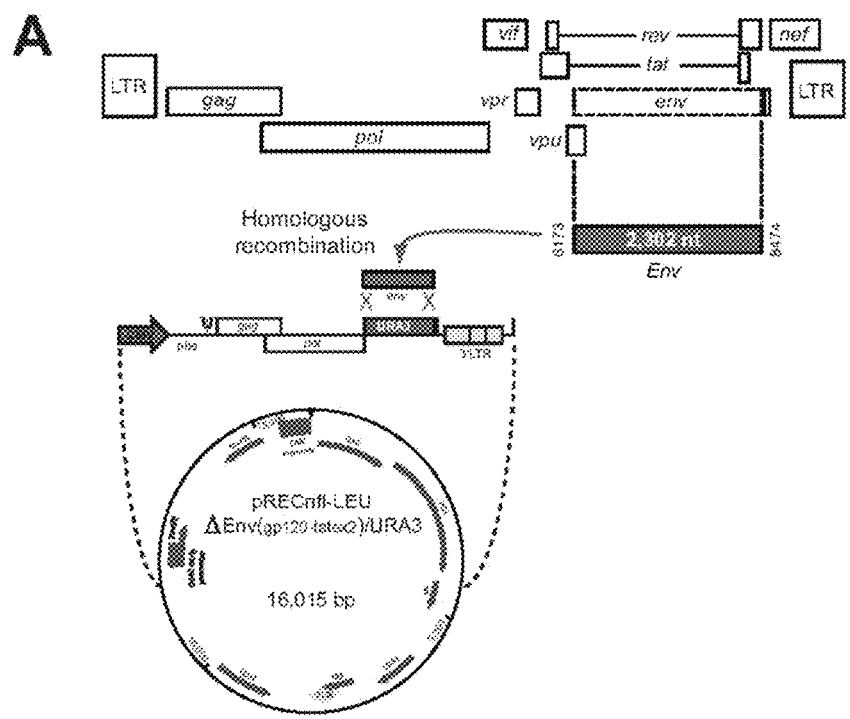
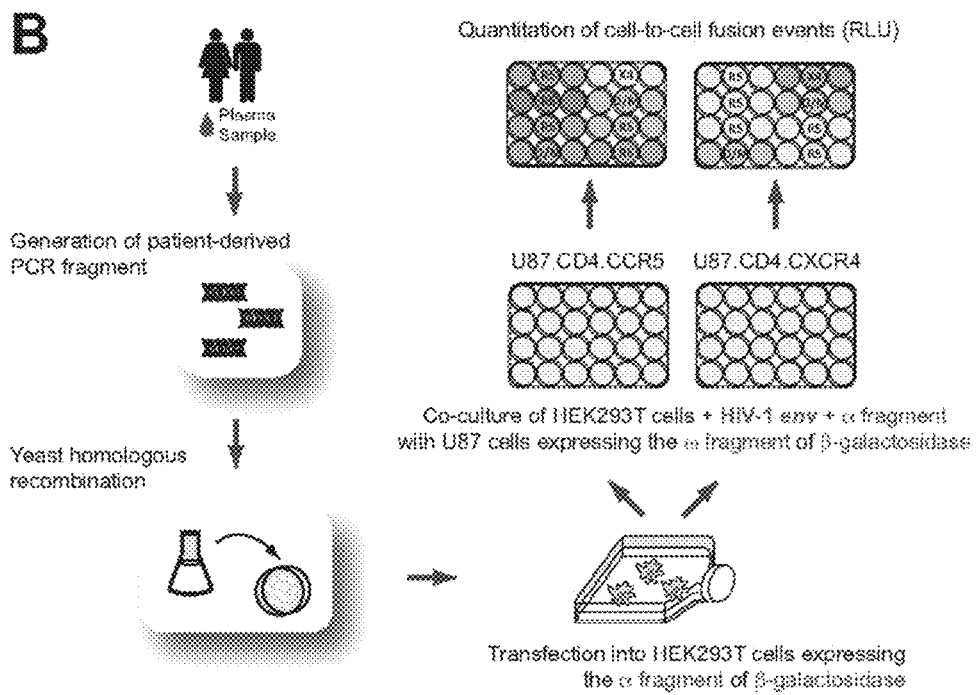
Figs. 1A-B

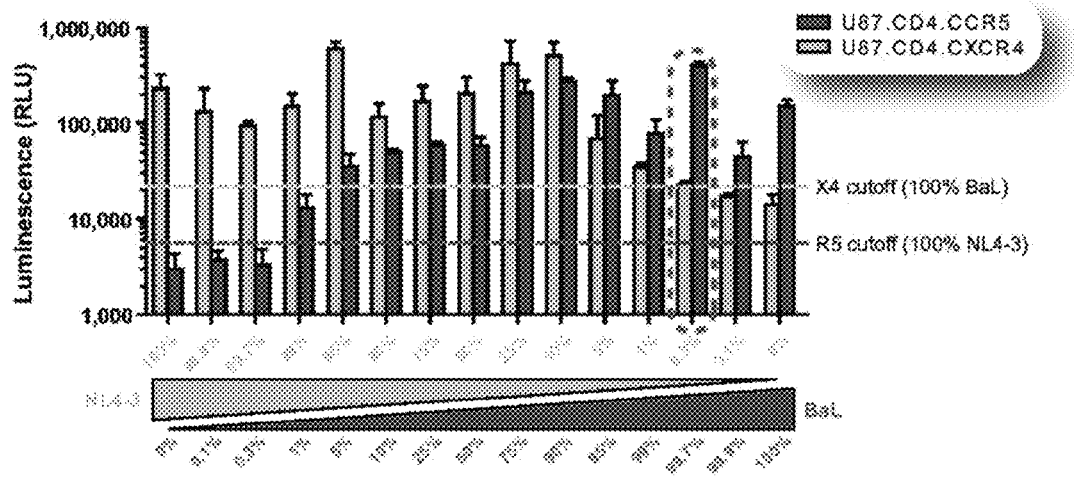
Figs. 3A-C

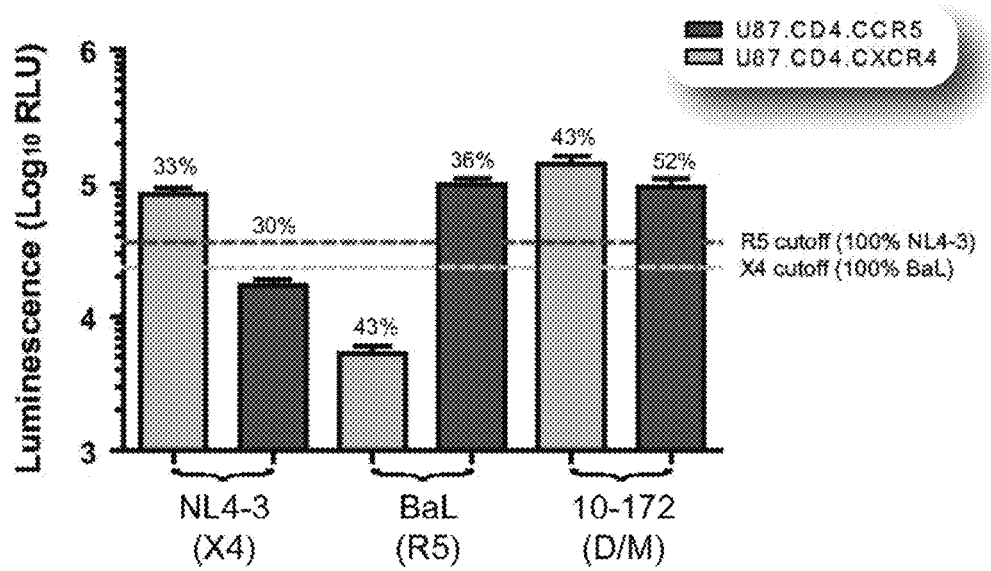
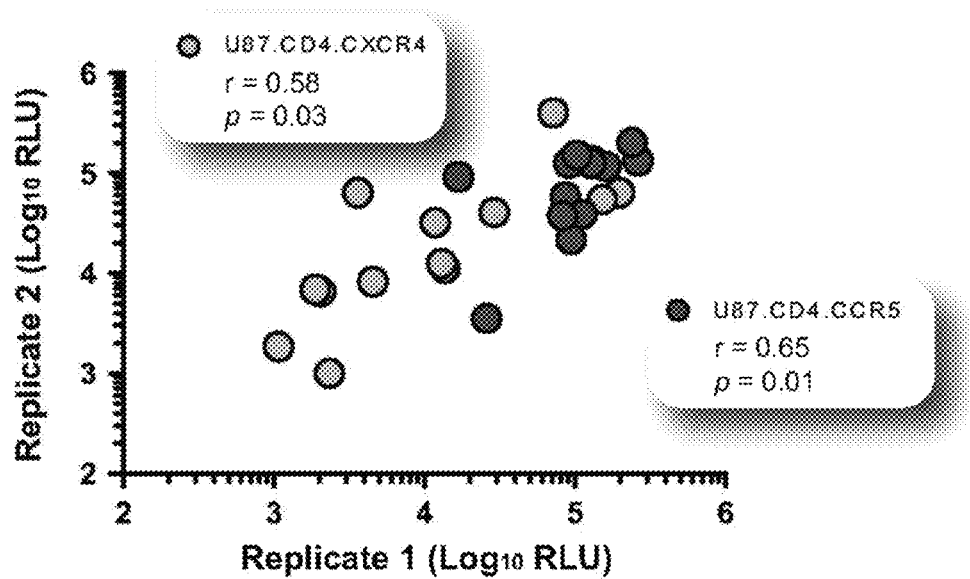
Figs. 4A-B

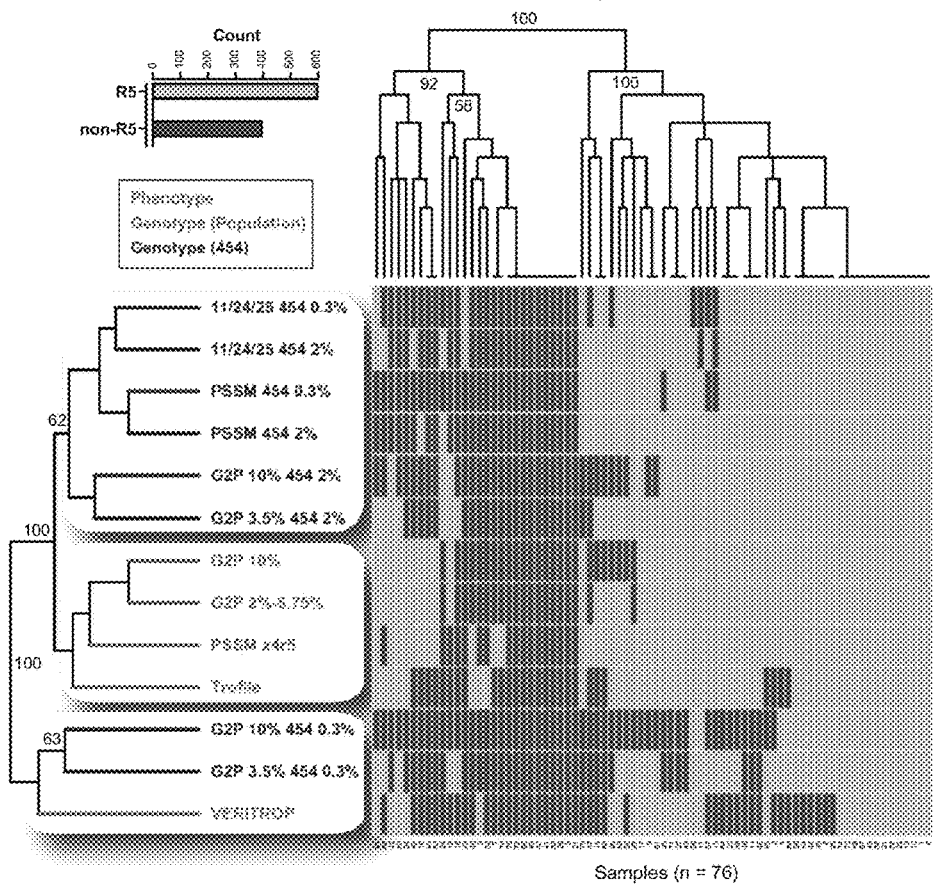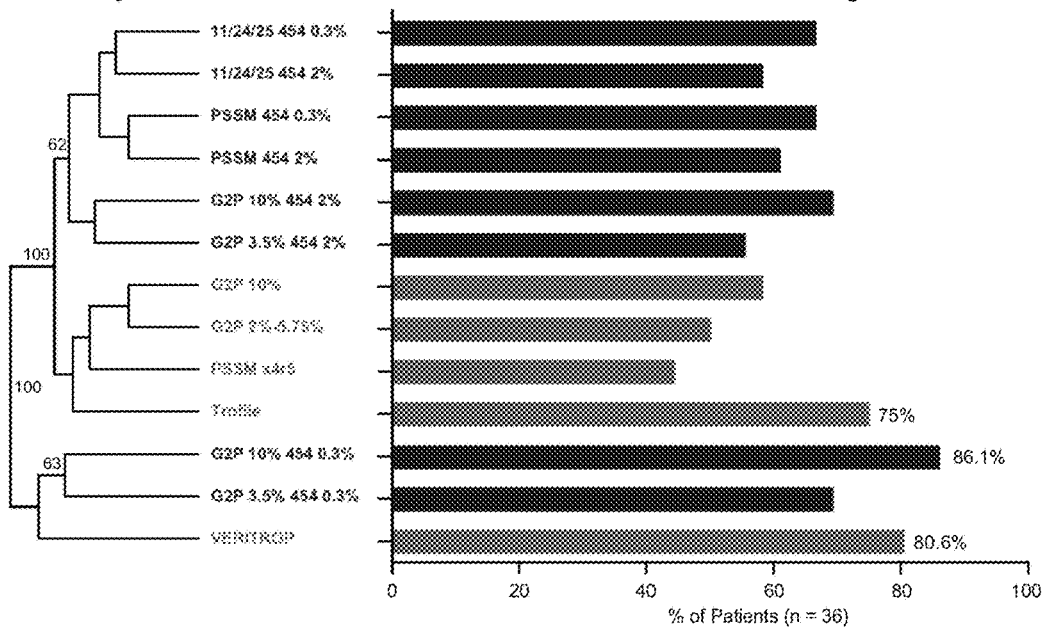
Figs. 5A-B

SEQUENCE LISTING

```
<160> NUMBER OF SEQ ID NOS: 14

<210> SEQ ID NO 1
<211> LENGTH: 50
<212> TYPE: DNA
<213> ORGANISM: Artificial Sequence
<220> FEATURE:
<223> OTHER INFORMATION: Oligonucleotide - HIV-1
<220> FEATURE:
<221> NAME/KEY: R=A+G
<222> LOCATION: (32)..(41)
<220> FEATURE:
<221> NAME/KEY: H=A+T+C
<222> LOCATION: (34)..(34)
<220> FEATURE:
<221> NAME/KEY: M=A+C
<222> LOCATION: (39)..(39)
<220> FEATURE:
<221> NAME/KEY: Y=C+T
<222> LOCATION: (49)..(49)

<400> SEQUENCE: 1
catattagga cgtatagtta gtcctaggtg trahtatcma rcaggacaya                50

<210> SEQ ID NO 2
<211> LENGTH: 50
<212> TYPE: DNA
<213> ORGANISM: Artificial Sequence
<220> FEATURE:
<223> OTHER INFORMATION: Oligonucleotide - HIV-1
<220> FEATURE:
<221> NAME/KEY: H=A+T+C
<222> LOCATION: (31)..(31)
<220> FEATURE:
<221> NAME/KEY: R=A+G
<222> LOCATION: (39)..(44)
<220> FEATURE:
<221> NAME/KEY: Y=C+T
<222> LOCATION: (40)..(50)

<400> SEQUENCE: 2
ggcgaatagc tctataagct gcttgtaata httctatary yctrtctgty                50

<210> SEQ ID NO 3
<211> LENGTH: 50
<212> TYPE: DNA
<213> ORGANISM: Artificial Sequence
```

```
<220> FEATURE:
<223> OTHER INFORMATION: Oligonucleotide - HIV-1
<220> FEATURE:
<221> NAME/KEY: Y=C+T
<222> LOCATION: (32)..(48)
<220> FEATURE:
<221> NAME/KEY: R=A+G
<222> LOCATION: (33)..(33)
<220> FEATURE:
<221> NAME/KEY: N=A+C+G+T
<222> LOCATION: (40)..(40)
<220> FEATURE:
<221> NAME/KEY: misc_feature
<222> LOCATION: (40)..(40)
<223> OTHER INFORMATION: n is a, c, g, or t

<400> SEQUENCE: 3
actgctatgg ctgtggcatt gagcaagtta ayrgcactan tyttyagytc                50

<210> SEQ ID NO 4
<211> LENGTH: 50
<212> TYPE: DNA
<213> ORGANISM: Artificial Sequence
<220> FEATURE:
<223> OTHER INFORMATION: Oligonucleotide - HIV-1
<220> FEATURE:
<221> NAME/KEY: R=A+G
<222> LOCATION: (31)..(50)
<220> FEATURE:
<221> NAME/KEY: Y=C+T
<222> LOCATION: (34)..(49)
<220> FEATURE:
<221> NAME/KEY: W=A+T
<222> LOCATION: (42)..(42)

<400> SEQUENCE: 4
agccataata agaattctgc aacaactgct rttyryycat twyagratyr                50

<210> SEQ ID NO 5
<211> LENGTH: 50
<212> TYPE: DNA
<213> ORGANISM: Artificial Sequence
<220> FEATURE:
<223> OTHER INFORMATION: Oligonucleotide - HIV-1
<220> FEATURE:
<221> NAME/KEY: B=T+C+G
<222> LOCATION: (37)..(37)
<220> FEATURE:
<221> NAME/KEY: Y=C+T
<222> LOCATION: (38)..(46)
<220> FEATURE:
<221> NAME/KEY: K=T+G
<222> LOCATION: (47)..(47)

<400> SEQUENCE: 5
agtgctaagg atccgttcac taatcgaatg gatctgbyty tgyctykctc                50

<210> SEQ ID NO 6
<211> LENGTH: 20
<212> TYPE: DNA
<213> ORGANISM: Artificial Sequence
<220> FEATURE:
<223> OTHER INFORMATION: Oligonucleotide - HIV-1

<400> SEQUENCE: 6
ccaggagcga cactagaaga                                                  20

<210> SEQ ID NO 7
<211> LENGTH: 50
<212> TYPE: DNA
<213> ORGANISM: Artificial Sequence
```

<220> FEATURE:
<223> OTHER INFORMATION: Oligonucleotide - HIV-1
<220> FEATURE:
<221> NAME/KEY: Y=C+T
<222> LOCATION: (34)..(48)
<220> FEATURE:
<221> NAME/KEY: N=A+C+G+T
<222> LOCATION: (35)..(35)
<220> FEATURE:
<221> NAME/KEY: misc_feature
<222> LOCATION: (35)..(35)
<223> OTHER INFORMATION: n is a, c, g, or t
<220> FEATURE:
<221> NAME/KEY: K=T+G
<222> LOCATION: (36)..(36)
<220> FEATURE:
<221> NAME/KEY: R=A+G
<222> LOCATION: (41)..(47)
<220> FEATURE:
<221> NAME/KEY: D=A+T+G
<222> LOCATION: (44)..(50)
<220> FEATURE:
<221> NAME/KEY: H=A+T+C
<222> LOCATION: (45)..(45)

<400> SEQUENCE: 7
atacttgggc aggagtggaa gccataataa gaaynktgca rcadhtrytd        50

<210> SEQ ID NO 8
<211> LENGTH: 50
<212> TYPE: DNA
<213> ORGANISM: Artificial Sequence
<220> FEATURE:
<223> OTHER INFORMATION: Oligonucleotide - HIV-1
<220> FEATURE:
<221> NAME/KEY: R=A+G
<222> LOCATION: (33)..(38)
<220> FEATURE:
<221> NAME/KEY: Y=C+T
<222> LOCATION: (37)..(49)
<220> FEATURE:
<221> NAME/KEY: N=A+C+G+T
<222> LOCATION: (39)..(39)
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: H=A+T+C
<222> LOCATION: (44)..(45)
<220> FEATURE:
<221> NAME/KEY: M=A+C
<222> LOCATION: (50)..(50)

<400> SEQUENCE: 8
aacctataat agtagcaata gtagcattag tartagyrnt aathhtagym        50

<210> SEQ ID NO 9
<211> LENGTH: 50
<212> TYPE: DNA
<213> ORGANISM: Artificial Sequence
<220> FEATURE:
<223> OTHER INFORMATION: Oligonucleotide - HIV-1
<220> FEATURE:
<221> NAME/KEY: N=A+C+G+T
<222> LOCATION: (31)..(32)
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: Y=C+T
<222> LOCATION: (35)..(38)
<220> FEATURE:
<221> NAME/KEY: M=A+C

```
<222> LOCATION: (39)..(39)
<220> FEATURE:
<221> NAME/KEY: R=A+G
<222> LOCATION: (41)..(48)
<220> FEATURE:
<221> NAME/KEY: H=A+T+C
<222> LOCATION: (47)..(47)

<400> SEQUENCE: 9
tgctgtttat ccatttcaga attgggtgtc nncayagymg ratagghrtt          50

<210> SEQ ID NO 10
<211> LENGTH: 50
<212> TYPE: DNA
<213> ORGANISM: Artificial Sequence
<220> FEATURE:
<223> OTHER INFORMATION: Oligonucleotide - HIV-1
<220> FEATURE:
<221> NAME/KEY: Y=C+T
<222> LOCATION: (32)..(44)
<220> FEATURE:
<221> NAME/KEY: K=T+G
<222> LOCATION: (33)..(49)

<400> SEQUENCE: 10
gttcactaat cgaatggatc tgtctctgtc tykctckcca yctycttckt          50

<210> SEQ ID NO 11
<211> LENGTH: 50
<212> TYPE: DNA
<213> ORGANISM: Artificial Sequence
<220> FEATURE:
<223> OTHER INFORMATION: Oligonucleotide - HIV-1
<220> FEATURE:
<221> NAME/KEY: Y=C+T
<222> LOCATION: (33)..(48)
<220> FEATURE:
<221> NAME/KEY: K=T+G
<222> LOCATION: (37)..(41)

<400> SEQUENCE: 11
atccgttcac taatcgaatg gatctgtctc tgyctykctc kccayctyct          50

<210> SEQ ID NO 12
<211> LENGTH: 20
<212> TYPE: DNA
<213> ORGANISM: Artificial Sequence
<220> FEATURE:
<223> OTHER INFORMATION: Oligonucleotide - HIV-1

<400> SEQUENCE: 12
gacaggttaa ttgatagact                                           20

<210> SEQ ID NO 13
<211> LENGTH: 17020
<212> TYPE: DNA
<213> ORGANISM: Artificial Sequence
<220> FEATURE:
<223> OTHER INFORMATION: Plasmid sequence containing HIV-1, E-coli, and
      yeast sequences

<400> SEQUENCE: 13
agtggcgccc gaacagggac ttgaaagcga agtaaagcc agaggagatc tctcgacgca    60
ggactcggct tgctgaagcg cgcacggcaa gaggcgaggg gcggcgactg gtgagtacgc  120
caaaaatttt gactagcgga ggctagaagg agagagatgg gtgcgagagc gtcggtatta  180
agcgggggag aattagataa atgggaaaaa attcggttaa ggccaggggg aagaaacaa   240
```

```
tataaactaa aacatatagt atgggcaagc agggagctag aacgattcgc agttaatcct    300
ggccttttag agacatcaga aggctgtaga caaatactgg acagctaca accatccctt    360
cagacaggat cagaagaact tagatcatta taatacaa tagcagtcct ctattgtgtg     420
catcaaagga tagatgtaaa agacaccaag gaagccttag ataagataga ggaagagcaa   480
aacaaaagta agaaaaaggc acagcaagca gcagctgaca caggaaacaa cagccaggtc   540
agccaaaatt accctatagt gcagaacctc caggggcaaa tggtacatca ggccatatca   600
cctagaactt taaatgcatg ggtaaaagta gtagaagaga aggctttcag cccagaagta   660
atacccatgt tttcagcatt atcagaagga gccaccccac aagatttaaa taccatgcta   720
aacacagtgg ggggacatca agcagccatg caaatgttaa aagagaccat caatgaggaa   780
gctgcagaat gggatagatt gcatccagtg catgcagggc ctattgcacc aggccagatg   840
agagaaccaa ggggaagtga catagcagga actactagta cccttcagga caaataggat   900
ggatgacac ataatccacc tatcccagta ggagaaatct ataaaagatg gataatcctg      960
ggattaaata aaatagtaag aatgtatagc cctaccagca ttctggacat aagacaagga  1020
ccaaaggaac cctttagaga ctatgtagac cgattctata aaactctaag agccgagcaa  1080
gcttcacaag aggtaaaaaa ttggatgaca gaaaccttgt tggtccaaaa tgcgaaccca  1140
gattgtaaga ctattttaaa agcattggga ccaggagcga cactagaaga atgatgaca   1200
gcatgtcagg gagtggggggg acccggccat aaagcaagag ttttggctga gcaatgagc  1260
caagtaacaa atccagctac cataatgata cagaaaggca attttaggaa ccaaagaaag  1320
actgttaagt gtttcaattg tggcaaagaa gggcacatag ccaaaaattg cagggcccct  1380
aggaaaaagg gctgttggaa atgtggaaag gaaggacacc aaatgaaaga ttgtactgag  1440
agacaggcta ttttttagg gaagatctgg ccttcccaca agggaaggcc agggaatttt  1500
cttcagagca gaccagagcc aacagcccca ccagaagaga gcttcaggtt tggggaagag  1560
acaacaactc cctctcagaa gcaggagccg atagacaagg aactgtatcc tttagcttcc  1620
ctcagatcac tctttggcag cgaccccctc gtcacaataa agatagggggg caattaaagg  1680
aagctctatt agatacagga gcagatgata cagtattaga agaaatgaat ttgccaggaa  1740
gatggaaacc aaaaatgata gggggaattg gaggttttat caaagtagga cagtatgatc  1800
agatactcat agaaatctgc ggacataaag ctataggtac agtattagta ggacctacac  1860
ctgtcaacat aattggaaga aatctgttga ctcagattgg ctgcacttta aattttccca  1920
ttagtcctat tgagactgta ccagtaaaat taaagccagg aatggatggc ccaaaagtta  1980
aacaatggcc attgacagaa gaaaaaataa aagcattagt agaaatttgt acagaaatgg  2040
aaaaggaagg aaaaatttca aaaattgggc ctgaaaatcc atacaatact ccagtatttg  2100
ccataaagaa aaaagacagt actaaatgga gaaaattagt agatttcaga gaacttaata  2160
agagaactca gatttctgg gaagttcaat taggaatacc acatcctgca gggttaaaac  2220
agaaaaaatc agtaacagta ctggatgtgg gcgatgcata ttttcagtt cccttagata  2280
aagacttcag gaagtatact gcatttacca tacctagtat aaacaatgag acaccaggga  2340
ttagatatca gtacaatgtg cttccacagg gatggaaagg atcaccagca atattccagt  2400
gtagcatgac aaaaatctta gagcctttta gaaaacaaaa tccagacata gtcatctatc  2460
aatacatgga tgatttgtat gtaggatctg acttagaaat agggcagcat agaacaaaaa  2520
tagaggaact gagacaacat ctgttgaggt ggggatttac cacaccagac aaaaaacatc  2580
agaaagaacc tccattcctt tggatgggtt atgaactcca tcctgataaa tggacagtac  2640
```

```
agcctatagt gctgccagaa aaggacagct ggactgtcaa tgacatacag aaattagtgg    2700
gaaaattgaa ttgggcaagt cagatttatg cagggattaa agtaaggcaa ttatgtaaac    2760
ttcttagggg aaccaaagca ctaacagaag tagtaccact aacagaagaa gcagagctag    2820
aactggcaga aaacagggag attctaaaag aaccggtaca tggagtgtat tatgacccat    2880
caaaagactt aatagcagaa atacagaagc aggggcaagg ccaatggaca tatcaaattt    2940
atcaagagcc atttaaaaat ctgaaaacag gaaaatatgc aagaatgaag ggtgcccaca    3000
ctaatgatgt aaaacaatta acagaggcag tacaaaaaat agccacagaa agcatagtaa    3060
tatggggaaa gactcctaaa tttaaattac ccatacaaaa ggaaacatgg gaagcatggt    3120
ggacagagta ttggcaagcc acctggattc ctgagtggga gtttgtcaat acccctccct    3180
tagtgaagtt atggtaccag ttagagaaag aacccataat aggagcagaa actttctatg    3240
tagatggggc agccaatagg gaaactaaat taggaaaagc aggatatgta actgacagag    3300
gaagacaaaa agttgtcccc ctaacggaca caacaaatca gaagactgag ttacaagcaa    3360
ttcatctagc tttgcaggat tcgggattag aagtaaacat agtgacagac tcacaatatg    3420
cattgggaat cattcaagca caaccagata agagtgaatc agagttagtc agtcaaataa    3480
tagagcagtt aataaaaaag gaaaaagtct acctggcatg ggtaccagca cacaaaggaa    3540
ttggaggaaa tgaacaagta gatgggttgg tcagtgctgg aatcaggaaa gtactatttt    3600
tagatggaat agataaggcc caagaagaac atgagaaata tcacagtaat ggagagcaa    3660 tggctagtga ttttaaccta ccacctgtag tagcaaaaga aatagtagcc agctgtgata    3720
aatgtcagct aaaaggggaa gccatgcatg gacaagtaga ctgtagccca ggaatatggc    3780
agctagattg tacacattta gaaggaaaag ttatcttggt agcagttcat gtagccagtg    3840
gatatataga agcagaagta attccagcag agacagggca agaaacagca tacttcctct    3900
taaaattagc aggaagatgg ccagtaaaaa cagtacatac agacaatggc agcaatttca    3960
ccagtactac agttaaggcc gcctgttggt gggcggggat caagcaggaa tttggcattc    4020
cctacaatcc ccaaagtcaa ggagtaatag aatctatgaa taaagaatta aagaaaatta    4080
taggacaggt aagagatcag gctgaacatc ttaagacagc agtacaaatg gcagtattca    4140
tccacaattt taaaagaaaa ggggggattg ggggtacag tgcagggga agaatagtag    4200 acataatagc aacagacata caaactaaag aattacaaaa acaaattaca aaaattcaaa    4260
attttcgggt ttattacagg gacagcagag atccagtttg gaaaggacca gcaaagctcc    4320
tctggaaagg tgaaggggca gtagtaatac aagataatag tgcataaaa gtagtgccaa    4380 gaagaaaagc aaagatcatc agggattatg gaaaacagat ggcaggtgat gattgtgtgg    4440
caagtagaca ggatgaggat taacacatgg aaaagattag taaaacacca tatgtatatt    4500
tcaaggaaag ctaaggactg gttttataga catcactatg aaagtactaa tccaaaaata    4560
agttcagaag tacacatccc actaggggat gctaaattag taataacaac atattggggt    4620
ctgcatacag gagaaagaga ctggcatttg ggtcagggag tctccataga atggaggaaa    4680
aagagatata gcacacaagt agaccctgac ctagcagacc aactaattca tctgcactat    4740
tttgattgtt tttcagaatc tgctataaga aataccatat taggacgtat agttagtcct    4800
aggtgtgaat atcaagcagg acataacaag gtaggatctc tacagtactt ggcactagca    4860
gcattaataa aaccaaaaca gataaagcca ccttttgccta gtgttaggaa actgacagag    4920
gacagatgga acaagcccca gaagaccaag ggccacagag ggagccatac aatgaatgga    4980
```

```
cactagagct tttagaggaa cttaagagtg aagctgttag acattttcct aggatatggc    5040
tccataactt aggacaacat atctatgaaa cttacgggga tacttgggca ggagtggaag    5100
ccataataag aattctgcaa caactgctgt ttatccattt cagaattggg tgtcgacata    5160
gcagaatagg cgttactcga cagaggagag caagaaatgg agccagtaga tcctagacta    5220
gagccctgga agcatccagg aagtcagcct aaaactgctt gtaccaattg ctattgtaaa    5280
aagtgttgct ttcattgcca agtttgtttc atgacaaaag ccttaggcat ctcctatggc    5340
aggaagaagc ggagacagcg acgaagagct catcagaaca gtcagactca tcaagcttct    5400
ctatcaaagc agtaagtagt acatgtaatg caacctataa tagtagcaat agtagcatta    5460
gtagtagcaa taataatagc aatagttgtg tggtccatag taatcataga atataggaaa    5520
atattaagac aaagaaaaat agacaggtta attgatagac taatagaaag agcagaagac    5580
agtggcaatg agagtgaagg agaagtatca gcacttgtgg agatgggggt ggaaatgggg    5640
caccatgctc cttgggatat tgatgatctg tagtgctaca gaaaaattgt gggtcacagt    5700
ctattatggg gtacctgtgt ggaaggaagc aaccaccact ctattttgtg catcagatgc    5760
taaagcatat gatacagagg tacataatgt ttgggccaca catgcctgtg tacccacaga    5820
ccccaaccca caagaagtag tattggtaaa tgtgacagaa aattttaaca tgtggaaaaa    5880
tgacatggta aacagatgc atgaggatat aatcagttta tgggatcaaa gcctaaagcc    5940
atgtgtaaaa ttaaccccac tctgtgttag tttaaagtgc actgatttga agaatgatac    6000
taataccaat agtagtagcg ggagaatgat aatggagaaa ggagagataa aaaactgctc    6060
tttcaatatc agcacaagca taagagataa ggtgcagaaa gaatatgcat tcttttataa    6120
acttgatata gtaccaatag ataataccag ctataggttg ataagttgta cacctcagt    6180 cattacacag gcctgtccaa aggtatcctt tgagccaatt cccatacatt attgtgcccc    6240
ggctggtttt gcgattctaa aatgtaataa taagacgttc aatggaacag gaccatgtac    6300
aaatgtcagc acagtacaat gtacacatgg aatcaggcca gtagtatcaa ctcaactgct    6360
gttaaatggc agtctagcag aagaagatgt agtaattaga tctgccaatt tcacagacaa    6420
tgctaaaacc ataatagtac agctgaacac atctgtagaa attaattgta caagacccaa    6480
caacaataca agaaaaagta tccgtatcca gaggggacca gggagagcat tgttacaat    6540 aggaaaaata ggaaatatga gacaagcaca ttgtaacatt agtagagcaa atggaatgc    6600 cactttaaaa cagatagcta gcaaattaag agaacaattt ggaaataata aacaataat    6660 ctttaagcaa tcctcaggag gggacccaga aattgtaacg cacagttta attgtggagg    6720 ggaattttc tactgtaatt caacacaact gtttaatagt acttggttta atagtacttg    6780
gagtactgaa gggtcaaata cactgaagg aagtgacaca atcacactcc catgcagaat    6840
aaaacaattt ataaacatgt ggcaggaagt aggaaaagca atgtatgccc ctcccatcag    6900
tggacaaatt agatgttcat caaatattac tgggctgcta ttaacaagag atggtggtaa    6960
taacaacaat gggtccgaga tcttcagacc tggaggaggc gatatgaggg acaattggag    7020
aagtgaatta tataaatata agtagtaaa aattgaacca ttaggagtag cacccaccaa    7080
ggcaaagaga agagtggtgc agagagaaaa aagagcagtg gaataggag ctttgttcct    7140 tgggttcttg ggagcagcag gaagcactat gggctgcacg tcaatgacgc tgacggtaca    7200
ggccagacaa ttattgtctg atatagtgca gcagcagaac aatttgctga ggctattga    7260 ggcgcaacag catctgttgc aactcacagt ctggggcatc aaacagctcc aggcaagaat    7320
cctggctgtg gaaagatacc taaaggatca acagctcctg gggatttggg gttgctctgg    7380
```

-continued

```
aaaactcatt tgcaccactg ctgtgccttg gaatgctagt tggagtaata aatctctgga    7440
acagatttgg aataacatga cctggatgga gtgggacaga gaaattaaca attacacaag    7500
cttaatacac tccttaattg aagaatcgca aaaccagcaa gaaaagaatg aacaagaatt    7560
attggaatta gataaatggg caagtttgtg gaattggttt aacataacaa attggctgtg    7620
gtatataaaa ttattcataa tgatagtagg aggcttggta ggtttaagaa tagttttgc    7680
tgtactttct atagtgaata gagttaggca gggatattca ccattatcgt ttcagaccca    7740
cctcccaatc ccgaggggac ccgacaggcc cgaaggaata aagaagaag gtggagagag    7800
agacagagac agatccattc gattagtgaa cggatcctta gcacttatct gggacgatct    7860
gcggagcctg tgcctcttca gctaccaccg cttgagagac ttactcttga ttgtaacgag    7920
gattgtggaa cttctgggac gcaggggtg ggaagccctc aaatattggt ggaatctcct    7980
acagtattgg agtcaggaac taaagaatag tgctgttaac ttgctcaatg ccacagccat    8040
agcagtagct gaggggacag atagggttat agaagtatta caagcagctt atagagctat    8100
tcgccacata cctagaagaa taagacaggg cttggaaagg attttgctat aagatgggtg    8160
gcaagtggtc aaaaagtagt gtgattggat ggcctgctgt aagggaaaga atgagacgag    8220
ctgagccagc agcagatggg gtgggagcag tatctcgaga cctagaaaaa catggagcaa    8280
tcacaagtag caatacagca gctaacaatg ctgcttgtgc ctggctagaa gcacaagagg    8340
aggaagaggt gggttttcca gtcacacctc aggtaccttt aagaccaatg acttacaagg    8400
cagctgtaga tcttagccac ttttttaaaag aaaagggggg actggaaggg ctaattcact    8460
cccaaagaag acaagatatc cttgatctgt ggatctacca cacacaaggc tacttccctg    8520
attggcagaa ctacacacca gggccagggg tcagatatcc actgacccttt ggatggtgct    8580
acaagctagt accagttgag ccagataagg tagaagaggc caataaagga gagaacacca    8640
gcttgttaca ccctgtgagc ctgcatggaa tggatgaccc tgagagagaa gtgttagagt    8700
ggaggtttga cagccgccta gcatttcatc acgtggcccg agagctgcat ccggagtact    8760
tcaagaactg ctgacatcga gcttgctaca agggactttc cgctgggac tttccaggga    8820
ggcgtggcct gggcgggact ggggagtggc gagccctcag atgctgcata taagcagctg    8880
cttttgcct gtactgggtc tctctggtta ccagatctt gagcctggga gctctctggc    8940
taactaggga acccactgct taagcctcaa taaagcttgc cttgagtgct tcaagtagtg    9000
tgtgcccgtc tgttgtgtga ctctggtaac tagagatccc tcagaccctt ttagtcagtg    9060
tggaaaatct ctagcactcg agtctagacc ctcgaggaga acttctagta tatccacata    9120
cctaatatta ttgccttatt aaaaatggaa tcccaacaat tacatcaaaa tccacattct    9180
cttcaaaatc aattgtcctg tacttccttg ttcatgtgtg ttcaaaaacg ttatattat    9240
aggataatta tactctattt ctcaacaagt aattggttgt ttggccgagc ggtctaaggc    9300
gcctgattca agaaatatct tgaccgcagt taactgtggg aatactcagg tatcgtaaga    9360
tgcaagagtt cgaatctctt agcaaccatt attttttttcc tcaacataac gagaacacac    9420
agggcgcta tcgcacagaa tcaaattcga tgactggaaa ttttttgtta atttcagagg    9480
tcgcctgacg catataacctt tttcaactga aaaattggga gaaaaggaa aggtgagagg    9540
ccggaaccgg cttttcatat agaatagaga agcgttcatg actaaatgct tgcatcacaa    9600
tacttgaagt tgcaatatat tttaaggac ctattgtttt ttccaatagg tggttagcaa    9660
tcgtcttact ttctaacttt tcttaccttt tacatttcag caatatatat atatatttca    9720
```

```
aggatatacc attctaatgt ctgcccctat gtctgcccct aagaagatcg tcgttttgcc   9780
aggtgaccac gttggtcaag aaatcacagc cgaagccatt aaggttctta aagctatttc   9840
tgatgttcgt tccaatgtca agttcgattt cgaaaatcat ttaattggtg gtgctgctat   9900
cgatgctaca ggtgtcccac ttccagatga ggcgctggaa gcctccaaga aggttgatgc   9960
cgttttgtta ggtgctgtgg gtggtcctaa atggggtacc ggtagtgtta gacctgaaca  10020
aggtttacta aaaatccgta aagaacttca attgtacgcc aacttaagac catgtaactt  10080
tgcatccgac tctcttttag acttatctcc aatcaagcca caatttgcta aaggtactga  10140
cttcgttgtt gtcagagaat tagtgggagg tatttacttt ggtaagagaa aggaagacga  10200
tggtgatggt gtcgcttggg atagtgaaca atacaccgtt ccagaagtgc aaagaatcac  10260
aagaatggcc gctttcatgg ccctacaaca tgagccacca ttgcctattt ggtccttgga  10320
taaagctaat gttttggcct cttcaagatt atggagaaaa actgtggagg aaaccatcaa  10380
gaacgaattc cctacattga aggttcaaca tcaattgatt gattctgccg ccatgatcct  10440
agttaagaac ccaaccccac taaatggtat tataatcacc agcaacatgt ttggtgatat  10500
catctccgat gaagcctccg ttatcccagg ttccttgggt ttgttgccat ctgcgtcctt  10560
ggcctctttg ccagacaaga acaccgcatt tggtttgtac gaaccatgcc acggttctgc  10620
tccagatttg ccaaagaata aggttgaccc tatcgccact atcttgtctg ctgcaatgat  10680
gttgaaattg tcattgaact tgcctgaaga aggtaaggcc attgaagatg cagttaaaaa  10740
ggttttggat gcaggtatca gaactggtga tttaggtggt tccaacagta ccaccgaagt  10800
cggtgatgct gtcgccgaag aagttaagaa aatccttgct taaaaagatt ctcttttttt  10860
atgatatttg tacataaact ttataaatga aattcataat agaaacgaca cgaaattaca  10920
aaatggaata tgttcatagg gtagacgaaa ctatatacgc aatctacata catttatcaa  10980
gaaggagaaa aaggaggata gtaaaggaat acaggtaagc aaattgatac taatggctca  11040
acgtgataag gaaaaagaat tgcactttaa cattaatatt gacaaggagg agggcaccac  11100
acaaaaagtt aggtgtaaca gaaaatcatg aaactacgat tcctaatttg atattggagg  11160
attttctcta aaaaaaaaaa aatacaacaa ataaaaaaca ctcaatgacc tgaccatttg  11220
atggagttta agtcaatacc ttcttgaacc atttcccata atggtgaaag ttccctcaag  11280
aattttactc tgtcagaaac ggccttacga cgtagtcgat atggtgcact ctcagtacaa  11340
tctgctctga tgccgcatag ttaagccagc cccgacaccc gccaacaccc gctgacgcgc  11400
cctgacgggc ttgtctgctc ccggcatccg cttacagaca agctgtgacc gtctccggga  11460
gctgcatgtg tcagaggttt tcaccgtcat caccgaaacg cgcgagacga agggcctcg  11520 tgatacgcct atttttatag gttaatgtca tgataataat ggtttcttag gacggatcgc  11580
ttgcctgtaa cttacacgcg cctcgtatct tttaatgatg gaataatttg ggaatttact  11640
ctgtgtttat ttattttat gttttgtatt tggattttag aaagtaaata aagaaggtag  11700
aagagttacg gaatgaagaa aaaaaaataa acaaaggttt aaaaaatttc aacaaaaagc  11760
gtactttaca tatatattta ttagacaaga aaagcagatt aaatagatat acattcgatt  11820
aacgataagt aaaatgtaaa atcacaggat tttcgtgtgt ggtcttctac acagacaaga  11880
tgaaacaatt cggcattaat acctgagagc aggaagagca agataaaagg tagtatttgt  11940
tggcgatccc cctagagtct tttacatctt cggaaaacaa aaactatttt ttctttaatt  12000 tctttttta ctttctatttt ttaatttata tatttatatt aaaaaattta aattataatt  12060
atttttatag cacgtgatga aaaggaccca ggtggcactt ttcggggaaa tgtgcgcgga  12120
```

```
accectattt gtttattttt ctaaatacat tcaaatatgt atccgctcta gagggcccgt    12180
ttaaacccgc tgatcagcct cgactgtgcc ttctagttgc cagccatctg ttgtttgccc    12240
ctcccccgtg ccttccttga ccctggaagg tgccactccc actgtccttt cctaataaaa    12300
tgaggaaatt gcatcgcatt gtctgagtag gtgtcattct attctggggg gtggggtggg    12360
gcaggacagc aaggggagg attgggaaga caatagcagg catgctgggg atgcggtggg     12420
ctctatggct tctgaggcgg aaagaaccag ctggggctct aggggtatc cccacgcgcc     12480
ctgtagcggc gcattaagcg cggcgggtgt ggtggttacg cgcagcgtga ccgctacact    12540
tgccagcgcc ctagcgcccg ctcctttcgc tttcttccct tcctttctcg ccacgttcgc    12600
cggctttccc cgtcaagctc taaatcgggg catcccttta gggttccgat ttagtgcttt    12660
acggcacctc gaccccaaaa aacttgatta gggtgatggt tcacgtagtg gccatcgcc     12720
ctgatagacg gtttttcgcc ctttgacgtt ggagtccacg ttctttaata gtggactctt    12780
gttccaaact ggaacaacac tcaaccctat ctcggtctat tcttttgatt tataagggat    12840
tttggggatt tcggcctatt ggttaaaaaa tgagctgatt taacaaaaat ttaacgcgaa    12900
ttaattctgt ggaatgtgtg tcagttaggg tgtggaaagt ccccaggctc cccaggcagg    12960
cagaagtatg caaagcatgc atctcaatta gtcagcaacc aggtgtggaa agtccccagg    13020
ctccccagca ggcagaagta tgcaaagcat gcatctcaat tagtcagcaa ccatagtccc    13080
gcccctaact ccgcccatcc cgcccctaac tccgcccagt tccgcccatt ctccgcccca    13140
tggctgacta ttttttttta tttatgcaga ggccgaggcc gcctctgcct ctgagctatt    13200
ccagaagtag tgaggaggct ttttggagg cctaggcttt tgcaaaaagc tcccgggagc     13260
ttgtatatcc attttcggat ctgatcagca cgtgttgaca attaatcatc ggcatagtat    13320
atcggcatag tataatacga caaggtgagg aactaaacca tggccaagtt gaccagtgcc    13380
gttccggtgc tcaccgcgcg cgacgtcgcc ggagcggtcg agttctggac cgaccggctc    13440
gggttctccc gggacttcgt ggaggacgac ttcgccggtg tggtccggga cgacgtgacc    13500
ctgttcatca gcgcggtcca ggaccaggtg gtgccggaca cacectggc ctgggtgtgg     13560
gtgcgcggcc tggacgagct gtacgccgag tggtcggagg tcgtgtccac gaacttccgg    13620
gacgcctccg gccggccat gaccgagatc ggcgagcagc cgtggggcg ggagttcgcc      13680
ctgcgcgacc cggccggcaa ctgcgtgcac ttcgtggccg aggagcagga ctgacacgtg    13740
ctacgagatt tcgattccac cgccgccttc tatgaaaggt tgggcttcgg aatcgttttc    13800
cgggacgccg gctggatgat cctccagcgc ggggatctca tgctggagtt cttcgcccac    13860
cccaacttgt ttattgcagc ttataatggt tacaaataaa gcaatagcat cacaaatttc    13920
acaaataaag cattttttc actgcattct agttgtggtt tgtccaaact catcaatgta     13980
tcttatcatg tctgtatacc gtcgacctct agctagagct tggcgtaatc atggtcatag    14040
ctgtttcctg tgtgaaattg ttatccgctc acaattccac acaacatacg agccggaagc    14100
ataaagtgta aagcctgggg tgcctaatga gtgagctaac tcacattaat tgcgttgcgc    14160
tcactgcccg ctttccagtc gggaaacctg tcgtgccagc tgcattaatg aatcggccaa    14220
cgcgcgggga gaggcggttt gcgtattggg cgctcttccg cttcctcgct cactgactcg    14280
ctgcgctcgg tcgttcggct gcggcgagcg gtatcagctc actcaaaggc ggtaatacgg    14340
ttatccacag aatcagggga taacgcagga aagaacatgt gagcaaaagg ccagcaaaag    14400
gccaggaacc gtaaaaaggc cgcgttgctg gcgtttttcc ataggctccg ccccctgac     14460
```

```
gagcatcaca aaaatcgacg ctcaagtcag aggtggcgaa acccgacagg actataaaga    14520
taccaggcgt ttccccctgg aagctccctc gtgcgctctc ctgttccgac cctgccgctt    14580
accggatacc tgtccgcctt tctcccttcg ggaagcgtgg cgctttctca atgctcacgc    14640
tgtaggtatc tcagttcggt gtaggtcgtt cgctccaagc tgggctgtgt gcacgaaccc    14700
cccgttcagc ccgaccgctg cgccttatcc ggtaactatc gtcttgagtc caacccggta    14760
agacacgact tatcgccact ggcagcagcc actggtaaca ggattagcag agcgaggtat    14820
gtaggcggtg ctacagagtt cttgaagtgg tggcctaact acggctacac tagaaggaca    14880
gtatttggta tctgcgctct gctgaagcca gttaccttcg aaaaagagt tggtagctct    14940 tgatccggca acaaaccac cgctggtagc ggtggttttt ttgtttgcaa gcagcagatt    15000
acgcgcagaa aaaaggatc tcaagaagat cctttgatct tttctacggg gtctgacgct    15060
cagtggaacg aaaactcacg ttaagggatt ttggtcatga gattatcaaa aaggatcttc    15120
acctagatcc ttttaaatta aaaatgaagt tttaaatcaa tctaaagtat atatgagtaa    15180
acttggtctg acagttacca atgcttaatc agtgaggcac ctatctcagc gatctgtcta    15240
tttcgttcat ccatagttgc ctgactcccc gtcgtgtaga taactacgat acgggagggc    15300
ttaccatctg gccccagtgc tgcaatgata ccgcgagacc cacgctcacc ggctccagat    15360
ttatcagcaa taaaccagcc agccggaagg gccgagcgca gaagtggtcc tgcaacttta    15420
tccgcctcca tccagtctat taattgttgc cgggaagcta gagtaagtag ttcgccagtt    15480
aatagtttgc gcaacgttgt tgccattgct acaggcatcg tggtgtcacg ctcgtcgttt    15540
ggtatggctt cattcagctc cggttcccaa cgatcaaggc gagttacatg atccccatg    15600 ttgtgcaaaa aagcggttag ctccttcggt cctccgatcg ttgtcagaag taagttggcc    15660
gcagtgttat cactcatggt tatggcagca ctgcataatt ctcttactgt catgccatcc    15720
gtaagatgct tttctgtgac tggtgagtac tcaaccaagt cattctgaga atagtgtatg    15780
cggcgaccga gttgctcttg cccggcgtca atacggata ataccgcgcc acatagcaga    15840
actttaaaag tgctcatcat tggaaaacgt tcttcggggc gaaaactctc aaggatctta    15900
ccgctgttga atccagttc gatgtaaccc actcgtgcac ccaactgatc ttcagcatct    15960
tttactttca ccagcgtttc tgggtgagca aaaacaggaa ggcaaaatgc cgcaaaaaag    16020
ggaataaggg cgacacggaa atgttgaata ctcatactct tccttttca atattattga    16080 agcatttatc agggttattg tctcatgagc ggatacatat ttgaatgtat ttagaaaaat    16140
aaacaaatag gggttccgcg cacatttccc cgaaaagtgc cacctgacgt cgacggatcg    16200
ggagatctcc cgatcccta tggtcgactc tcagtacaat ctgctctgat gccgcatagt    16260
taagccagta tctgctccct gcttgtgtgt tggaggtcgc tgagtagtgc gcgagcaaaa    16320
tttaagctac aacaaggcaa ggcttgaccg acaattgcat gaagaatctg cttagggtta    16380
ggcgttttgc gctgcttcgc gatgtacggg ccagatatac gcgttgacat tgattattga    16440
ctagttatta atagtaatca attacggggt cattagttca tagcccatat atggagttcc    16500
gcgttacata acttacggta aatggcccgc ctggctgacc gcccaacgac ccccgcccat    16560
tgacgtcaat aatgacgtat gttcccatag taacgccaat agggactttc cattgacgtc    16620
aatgggtgga ctatttacgg taaactgccc acttggcagt acatcaagtg tatcatatgc    16680
caagtacgcc ccctattgac gtcaatgacg gtaaatggcc cgcctggcat tatgcccagt    16740
acatgacctt atgggacttt cctacttggc agtacatcta cgtattagtc atcgctatta    16800
ccatggtgat gcggttttgg cagtacatca atgggcgtgg atagcggttt gactcacggg    16860
```

```
gatttccaag tctccacccc attgacgtca atgggagttt gttttggcac caaaatcaac    16920
gggactttcc aaaatgtcgt aacaactccg ccccattgac gcaaatgggc ggtaggcgtg    16980
tacggtggga ggtctatata agcagagctc tctggctaac                          17020
```

<210> SEQ ID NO 14
<211> LENGTH: 50
<212> TYPE: DNA
<213> ORGANISM: Artificial Sequence
<220> FEATURE:
<223> OTHER INFORMATION: Synthetic Construct

<400> SEQUENCE: 14

```
tctctcaagc ggtggtagct gaagaggcac aggytcckba grtcgwccca               50
```

METHOD FOR DETECTING HIV-1 CO-RECEPTOR TROPISM

RELATED APPLICATION

This application claims priority from U.S. Provisional Application Nos. 61/771,401, filed Mar. 1, 2013 and 61/826,548, filed May 23, 2013, the subject matter of which are incorporated herein by reference in their entirety.

TECHNICAL FIELD

This application relates to a phenotypic assay for the determination of HIV-1 co-receptor tropism in a HIV-1 infected patient and to methods for predicting a patient's response to an HIV-1 treatment.

BACKGROUND

The entry of an enveloped virus into a target cell is initiated by the envelope protein of the virus binding to a receptor on the target cell membrane. The interaction of the receptor and the viral envelope protein triggers fusion between the envelope protein and the target cell membrane, permitting the entry of the viral genome into the cytoplasm of the target cell. The fusion mediated by the viral envelope protein also permits cell-to-cell transmission of enveloped viruses. The expression of the viral envelope protein on the membrane of an infected cell can trigger fusion with an uninfected cell bearing the appropriate viral envelope protein receptor, further increasing the virulence of the virus within the host. Thus, the receptor-viral envelope protein determines the tropism, virulence, and ultimately the pathogenicity of the virus in a particular host.

In HIV the viral envelope protein requires both a receptor and a co-receptor for the initiation of fusion events. The entry of HIV into target cells is mediated by a fusion reaction in which the gp120/gp41 glycoprotein of the virus binds to CD4 and a CC chemokine receptor, CCR5 or CXCR4, on the target cell membrane. The HIV enveloped surface glycoproteins are synthesized as a single 160 kD precursor protein which is cleaved by a cellular protease during viral budding into two glycoproteins, gp41 and gp120. gp41 is a transmembrane protein and gp120 is an extracellular protein which remains non-covalently associated with gp41, possibly in a trimeric or multimneic form.

The tropism and virulence of HIV appears to be determined by the co-receptor used to bind the viral envelope protein. HIV strains using the CCR5 as a co-receptor mediate transmission and predominate early in the course of disease, while those using CXCR4 are mainly associated with the symptomatic phase emerging in later disease stages and have been linked to a more rapid CD4+ T-cell depletion and progression to AIDS. Therefore, there remains a need for assays able to determine HIV-1 co-receptor usage, or tropism, that are quick, accurate and have the sensitivity required to detect minor non-R5 chemokine receptor variants.

SUMMARY

Described herein are compositions and methods useful for determining HIV-1 co-receptor tropism in an HIV-1 infected patient, methods for predicting a patient's response to an HIV-1 treatment, and methods of treating HIV-1 in a subject.

In some embodiments, a method for determining HIV-1 co-receptor tropism in an HIV-infected patient includes preparing an HIV-1 envelope protein coding sequence from a sample obtained that includes HIV-1 RNA from the patient. The HIV-1 envelope protein coding sequence is introduced into a first expression construct by providing a plasmid expression vector including a near-full length HIV-1 genome having a yeast uracil biosynthesis gene in place of an HIV-1 env coding sequence and replacing the yeast uracil biosynthesis gene with the HIV-1 envelope protein coding sequence prepared from the patient sample. A first cell is transfected with the first expression construct and a second expression construct. The second expression construct includes a first reporter molecule fragment coding sequence. The HIV-1 envelope protein and the first reporter molecule fragment are expressed on a cell surface of the first cell. A second cell that expresses a second reporter molecule fragment, an HIV-1 envelope protein receptor and an HIV-1 envelope protein co-receptor on a cell surface of the second cell is provided. The second reporter molecule fragment is capable of combining with first reporter molecule fragment to form a functional reporter molecule upon fusion of the first cell with the second cell. The first cell is then contacted with the second cell. The presence or absence of a signal produced by the functional reporter molecule is detected. The presence of a signal is indicative of the HIV-1 co-receptor tropism with the second cell.

In some embodiments, a blood plasma sample including HIV-1 viral RNA can be obtained from the HIV-infected subject.

In other embodiments, an HIV-1 envelope protein coding sequence from a sample obtained from the patient can be prepared by reverse transcribing the HIV-1 RNA to produce HIV-1 cDNA and amplifying a fragment of the HIV-1 cDNA. The amplified fragment can correspond to a portion of an HIV-1 envelope protein coding RNA sequence.

In other embodiments, the HIV-1 envelope protein coding sequence can be introduced into a first expression construct by providing a plasmid expression vector including a near-full length HIV-1 genome having a yeast uracil biosynthesis gene in place of a gp120/gp41 HIV-1 coding sequence and replacing the yeast uracil biosynthesis gene with the HIV-1 envelope protein coding sequence prepared from the patient sample.

In some embodiments, the second reporter molecule fragment can be expressed by transfecting the second cell with a third expression construct. The third expression construct can include a second reporter molecule fragment coding sequence encoding the second reported molecule.

In other embodiments, where the HIV-1 envelope protein receptor is CD4 and the HIV-1 envelope protein co-receptor is CXCR4, the presence of a signal compared to a control can be indicative of CXCR4 tropism in the HIV-infected patient. Alternatively, where the HIV-1 envelope protein receptor is CD4 and the HIV-1 envelope protein co-receptor is CCR5, the presence of a signal compared to a control can be indicative of CCR5 tropism in the HIV-infected patient.

In some embodiments, the first cell includes a HEK293T cell, and the second cell includes a U97 cell stably expressing CD4 and an HIV-1 viral envelope protein co-receptor. The HIV-1 viral envelope protein co-receptor is CCR5 or CXCR4.

In other embodiments, the first reporter molecule fragment and the second reporter molecule fragment are different from each other and are independently selected from an α-fragment of β-galactosidase and an ω-fragment of β-galactosidase. For example, the first reporter molecule fragment can express an α-fragment of β-galactosidase and the second reporter molecule fragment can express an ω-fragment of β-galactosidase.

In some embodiments, the HIV-1 envelope protein coding sequence can encode HIV gp120 and an N-terminal portion of gp41. In other embodiments, the HIV-1 envelope protein coding sequence does not encode a functional portion of the cytoplasmic domain of gp41.

In some embodiments, the first expression construct comprises a promoter operably linked to the HIV-1 envelope protein coding sequence from a sample prepared from the patient sample.

Other embodiments relate to a method of determining the susceptibility of HIV-1 infecting a patient to one or more anti-viral compounds and treating the subject based on the determined susceptibility. The method can include preparing an HIV-1 envelope protein coding sequence from a sample including HIV-1 RNA obtained from a patient infected with HIV-1. The HIV-1 envelope protein coding sequence is introduced into a first expression construct by providing a plasmid expression vector including a near-full length HIV-1 genome having a yeast uracil biosynthesis gene in place of a HIV-1 env coding sequence and replacing the yeast uracil biosynthesis gene with the HIV-1 envelope protein coding sequence prepared from the patient sample. A plurality of first cells is transfected with the first expression construct and a second expression construct. The second expression construct includes a first reporter molecule fragment coding sequence. The HIV-1 envelope protein and the first reporter molecule fragment are expressed on cell surfaces of the first cells. A plurality of second cells is provided that express a second reporter molecule fragment, CD4, and either CXCR4 or CCR5 on cell surfaces of the second cells. The second reporter molecule fragments are capable of combining with first reporter molecule fragments to form a functional reporter molecule upon fusion of the first cells with the second cells. The first cells are then contacted with the second cells. The presence or absence of a signal produced by the functional reporter molecules of the contacted first cell and second cells is then detected.

Where CD4 and CXCR4 are expressed by the second cells, a decreased signal compared to a control is indicative of the patient having an increased likelihood of a positive response to the CCR5 antagonist treatment and an increased signal compared to a control is indicative of the patient having a decreased likelihood of a positive response to the CCR5 antagonist treatment.

Alternatively, where CD4 and CCR5 are expressed by the second cells, a decreased signal compared to a control is indicative of the patient having an increased likelihood of a positive response to the CXCR4 antagonist treatment and an increased signal compared to a control is indicative of the patient having a decreased likelihood of a positive response to the CXCR4 antagonist treatment.

In some embodiments, where it is determined the subject will have an increased likelihood of a positive response to the CCR5 antagonist treatment, a therapeutically effective amount of a CCR5 antagonist can be administered to the subject.

In other embodiments, where it is determined the subject will have an increased likelihood of a positive response to the CXCR4 antagonist treatment, a therapeutically effective amount of a CXCR4 antagonist can be administered to the subject.

BRIEF DESCRIPTION OF THE DRAWINGS

The foregoing and other features of the present application will become apparent to those skilled in the art to which the present application relates upon reading the following description with reference to the accompanying drawings, in which:

FIGS. 1(A-B) illustrates: (A) a schematic drawing showing a method for introducing patient-derived env PCR fragments into an expression vector via yeast homologous recombination; and (B) a schematic drawing showing a HIV-1 co-receptor tropism assay (VERITROP) where patient-derived viral amplicons are introduced into a vector lacking the corresponding HIV-1 env sequence and co-transfected into HEK293T cells with a plasmid expression vector encoding the α fragment of the β-galactosidase gene (pCMVα). Cell-to-cell fusion events were quantified by transfecting the target cells (U87.CD4.CCR5 or U87.CD4.CXCR4) with a vector expressing the omega fragment (pCMVΩ) of the β-galactosidase gene and mixing them with the HIV-1 env+pCMVα expressing cells.

FIGS. 3(A-C) illustrate graphs showing luminescence of exemplary HIV-1 co-receptor tropism assays. The graphs illustrate the ability to detect minority non-R5 viruses within the HIV-1 population by mixing at different proportions: (A) plasmid DNA (HIV-1BaL and HIV-1NL4-3) prior to transfection of the HEK293T cells, (B) yeast colonies prior to plasmid DNA isolation (used to transfect HEK293T cells), and (C) HIV-1BaL and HIV-1NL4-3 DNA prior to PCR amplification. Bars denoting the minimal amount of non-R5 (X4) env detected with statistically significance (0.3%) are enclosed by a dashed line.

FIGS. 4(A-B) illustrate graphs showing the reproducibility of the HIV-1 co-receptor tropism assay. (A) env PCR products from three viruses with different and known HIV-1 co-receptor usage (X4, HIV-1NL4-3; R5, HIV-1BaL; and dual/mixed, HIV-110-172), were analyzed ten times (10× replicates), by three operators, with distinct lots of critical reagents over a 4-week period; and (B) reproducibility of the entire assay, starting from RNA extraction from 15 plasma samples from HIV-infected individuals, as determined by two different operators with different lots of critical reagents over a 14-day period.

FIGS. 5(A-B) illustrate graphs showing: (A) a comparison of the present HIV-1 co-receptor tropism assay with another phenotypic (Trofile) and two genotypic (population and 454 sequencing) assays; and (B) the ability of the different HIV-1 co-receptor tropism tests to predict the success of a maraviroc-based therapy was determined as the percentage of patients where non-R5 viruses were detected at baseline from the total number of patients who were not able to enter (due to the presence of non-R5 viruses at baseline as determined by Trofile) or failed to respond to the maraviroc-based regimen (n=36), i.e., % Treatment Success Prediction=((No. of patients with non-R5 viruses)/(No. of patients not entering or failing the maraviroc-based regimen (n=36)))×100. Values for the tests with the three highest percentages (best capability to predict the success of maraviroc based therapy) are indicated.

DETAILED DESCRIPTION

Figure 2:
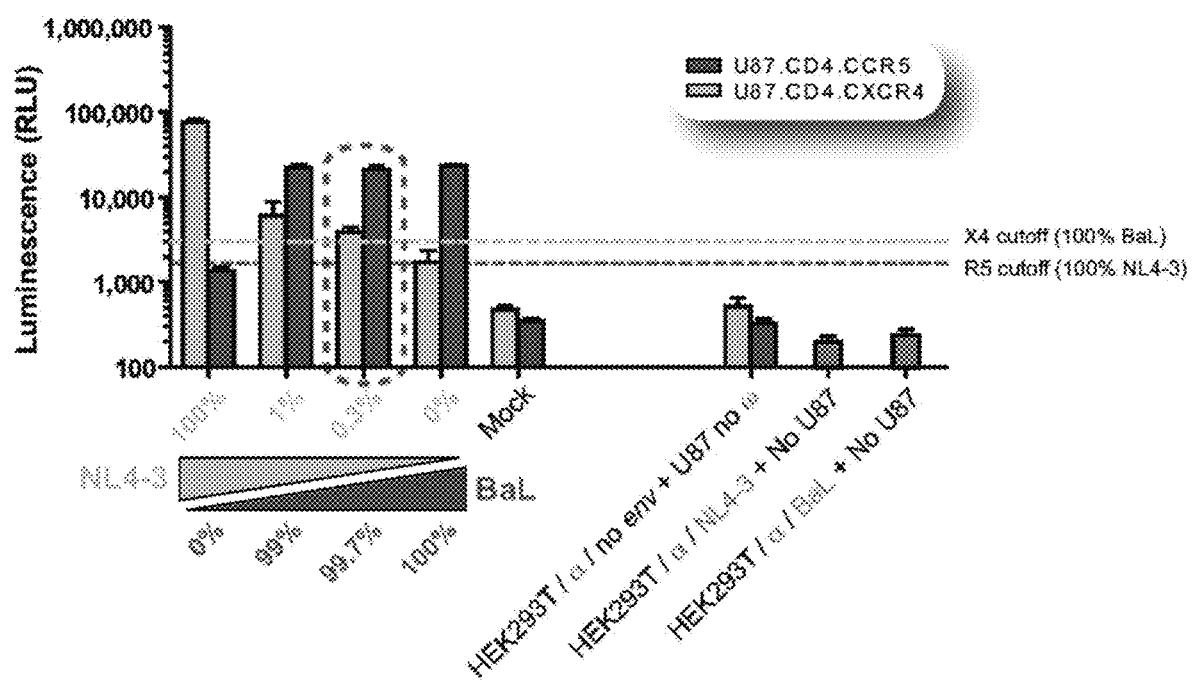
FIG. 2 illustrates a graph showing luminescence (relative light units (RLU)) using the HIV-1 co-receptor tropism assay of FIG. 1 for different amounts env amplicons from R5 (HIV-1BaL) and X4 (HIV-1NL4-3) mixed prior to cloning into the HIV-expression vector. Cell-to-cell fusion events were quantified including controls to take into account potential non-specific luminescence expression, i.e., (i) mock transfection, (ii) transfecting HEK293T cells with the α fragment but no env amplicon and target (U87) cells with no ω fragment, and (iii) HEK293T cells expressing HIV-1 env (R5 BaL or X4 NL4-3) with the α fragment in the total absence of target (U87) cells. The bar denoting the minimal amount of non-R5 (X4) env detected with statistically significance (0.3%) is enclosed by a dashed line.

It should be understood that the present invention is not limited to particular methods, reagents, compounds, compositions or biological systems, which can, of course, vary. It should also to be understood that the terminology used herein is for the purpose of describing particular aspects of the present invention only, and is not intended to be limiting. Unless defined otherwise, all technical and scientific terms used herein have the same meaning as commonly understood by one of ordinary skill in the art to which the present invention pertains. Although any methods and materials similar or equivalent to those described herein can be used in the practice of the present invention, the preferred materials and methods are described herein. In describing and claiming the present invention, the following terminology will be used.

The term "cell" and "cell line," refer to individual cells, harvested cells, and cultures containing the cells. A cell of the cell line is said to be "continuous," "immortal," or "stable" if the line remains viable over a prolonged time, typically at least about six months. To be considered a cell line, as used herein, the cells must remain viable for at least 50 passages. A "primary cell," or "normal cell," in contrast, refers to cells that do not remain viable over a prolonged time in culture.

The term "construct" refers to a recombinant nucleotide sequence, generally a recombinant nucleic acid molecule, that has been generated for the purpose of the expression of a specific nucleotide sequence(s), or is to be used in the construction of other recombinant nucleotide sequences.

The term "control", "control value" or "control signal" as used herein may refer to the compilation of data derived from samples of one or more individuals infected with HIV-1 classified as having a particular HIV-1 co-receptor tropism (e.g., CXCR4-tropic, and/or CCR5-tropic HIV-1). In some embodiments, the term "control" or "control value" can refer to a predetermined value or amount of signal generated by a functional reporter molecule that is indicative of a particular HIV-1 co-receptor tropism or ratio of CXCR4 and CCR5 tropic cells in a patient or patient sample. In some embodiments, the term "negative control" or "negative control value" can refer to a predetermined value or amount of signal generated by either the first or second fragment of a reporter molecule alone in a cell or group of cells. In some embodiments, the term "positive control" or "positive control value" can refer to a predetermined value or amount of signal generated by a complete functional reporter molecule in a cell or group of cells.

The term "exogenous" refers to a moiety that is added to a cell, either directly or by expression from a gene that is not present in wild-type cells. Included within this definition of "exogenous" are moieties that were added to a parent or earlier ancestor of a cell, and are present in the cell of interest as a result of being passed on from the parent cell. "Wild-type," in contrast, refers to cells that do not contain an exogenous moiety. "Exogenous DNA" includes DNA sequences that have one or more deletions, point mutations, and/or insertions, or combinations thereof, compared to DNA sequences in the wild-type target cell, as well as to DNA sequences that are not present in the wild-type cell or viral genome.

The term "gene" refers to a nucleic acid comprising a nucleotide sequence that encodes a polypeptide or a biologically active ribonucleic acid (RNA) such as a tRNA, shRNA, miRNA, etc. The nucleic acid can include regulatory elements (e.g., expression control sequences such as promoters, enhancers, an internal ribosome entry site (IRES)) and/or introns. A "gene product" or "expression product" of a gene is an RNA transcribed from the gene (e.g., pre- or post-processing) or a polypeptide encoded by an RNA transcribed from the gene (e.g., pre- or post-modification).

An "isolated" plasmid, nucleic acid, vector, virus, host cell, or other substance refers to a preparation of the substance devoid of at least some of the other components that may also be present where the substance or a similar substance naturally occurs or is initially prepared from. Thus, for example, an isolated substance may be prepared by using a purification technique to enrich it from a source mixture. Enrichment can be measured on an absolute basis, such as weight per volume of solution, or it can be measured in relation to a second, potentially interfering substance present in the source mixture. Increasing enrichments of the embodiments described herein are increasingly more isolated. An isolated plasmid, nucleic acid, vector, virus, host cell, or other substance is in some embodiments purified, e.g., from about 80% to about 90% pure, at least about 90% pure, at least about 95% pure, at least about 98% pure, or at least about 99%, or more, pure.

The term "nucleic acid" refers to polynucleotides such as DNA or RNA. Nucleic acids can be single-stranded, partly or completely, double-stranded, and in some cases partly or completely triple-stranded. Nucleic acids include genomic DNA, cDNA, mRNA, etc. Nucleic acids can be purified from natural sources, produced using recombinant expression systems and optionally purified, chemically synthesized, e.g., iRNA, siRNAs, microRNAs, and ribonucleoproteins. Where appropriate, e.g., in the case of chemically synthesized molecules, nucleic acids can comprise nucleoside analogs such as analogs having chemically modified bases or sugars, backbone modifications, etc. The term "nucleic acid sequence" as used herein can refer to the nucleic acid material itself and is not restricted to the sequence information (i.e., the succession of letters chosen among the five base letters A, G, C, T, or U) that biochemically characterizes a specific nucleic acid, e.g., a DNA or RNA molecule. A nucleic acid sequence is presented in the 5' to 3' direction unless otherwise indicated. The term "nucleic acid segment" is used herein to refer to a nucleic acid sequence that is a portion of a longer nucleic acid sequence.

The term "operably linked" refers to functional linkage between a nucleic acid expression control sequence (such as a promoter, or array of transcription factor binding sites) and a second nucleic acid sequence, wherein the expression control sequence directs transcription of the nucleic acid corresponding to the second sequence.

The terms "operably linked" and "operably associated" refer to a functional relationship between two nucleic acids, wherein the expression, activity, localization, etc., of one of the sequences is controlled by, directed by, regulated by, modulated by, etc., the other nucleic acid. The two nucleic acids are said to be operably linked or operably associated or in operable association. "Operably linked" or "operably associated" can also refer to a relationship between two polypeptides wherein the expression of one of the polypeptides is controlled by, directed by, regulated by, modulated by, etc., the other polypeptide. Typically a first nucleic acid sequence that is operably linked to a second nucleic acid sequence, or a first polypeptide that is operatively linked to a second polypeptide, is covalently linked, either directly or indirectly, to such a sequence, although any effective three-dimensional association is acceptable. One of ordinary skill in the art will appreciate that multiple nucleic acids, or multiple polypeptides, may be operably linked or associated with one another.

The term "plasmid" refers to a circular nucleic acid vector. Plasmids contain an origin of replication that allows many copies of the plasmid to be produced in a bacterial or eukaryotic cell (e.g., 293T producer cell) without integration of the plasmid into the host cell DNA.

The term "promoter" as used herein refers to a recognition site of a DNA strand to which the RNA polymerase binds. The promoter forms an initiation complex with RNA polymerase to initiate and drive transcriptional activity. The complex can be modified by activating sequences termed "enhancers" or inhibitory sequences termed "silencers".

The term "pharmaceutical composition" refers to a preparation of one or more of the agents described herein with other chemical components such as physiologically suitable carriers and excipients. The purpose of a pharmaceutical composition is to facilitate administration of an agent to a subject.

The term "plasmid" is meant a circular nucleic acid vector. Plasmids contain an origin of replication that allows many copies of the plasmid to be produced in a bacterial or eukaryotic cell (e.g., 293T producer cell) without integration of the plasmid into the host cell DNA.

The term "quantitative data" or "quantitative level" or "quantitative amount" as used herein refers to data, levels, or amounts associated with any dataset components (e.g., markers or clinical indicia) that can be assigned a numerical value.

The term "recombinant" refers to a nucleic acid sequence that comprises portions that do not naturally occur together as part of a single sequence or that have been rearranged relative to a naturally occurring sequence. A recombinant nucleic acid is created by a process that involves the hand of man and/or is generated from a nucleic acid that was created by hand of man (e.g., by one or more cycles of replication, amplification, transcription, etc.). A recombinant virus or viral particle is one that comprises a recombinant nucleic acid. A recombinant cell is one that comprises a recombinant nucleic acid.

The term "transfection" refers to the introduction of foreign DNA into eukaryotic cells. Transfection may be accomplished by a variety of means known in the art including but not limited to calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "transduction" refers to the delivery of a gene(s) using a viral or retroviral vector by means of viral infection rather than by transfection. In preferred embodiments, retroviral vectors are transduced by packaging the vectors into virions prior to contact with a cell. For example, an anti-HIV gene carried by a retroviral vector can be transduced into a cell through infection and provirus integration.

The term "promoter/enhancer" refers to a segment of DNA which contains sequences capable of providing both promoter and enhancer functions. For example, the long terminal repeats of retroviruses contain both promoter and enhancer functions. The enhancer/promoter may be "endogenous" or "exogenous" or "heterologous." An "endogenous" enhancer/promoter is one which is naturally linked with a given gene in the genome. An "exogenous" or "heterologous" enhancer/promoter is one which is placed in juxtaposition to a gene by means of genetic manipulation (i.e., molecular biological techniques) such that transcription of that gene is directed by the linked enhancer/promoter.

The term "vector" refers to an agent for transferring a nucleic acid (or nucleic acids) to a host cell. A vector comprises a nucleic acid that includes the nucleic acid fragment to be transferred, and optionally comprises a viral capsid or other materials for facilitating entry of the nucleic acid into the host cell and/or replication of the vector in the host cell (e.g., reverse transcriptase or other enzymes which are packaged within the capsid, or as part of the capsid).

The term "vector" or "vector construct" is used herein to refer to a nucleic acid molecule capable transferring or transporting another passenger DNA or RNA nucleic acid molecule (i.e., a sequence or gene of interest) into a host cell. For instance, either a DNA or RNA vector can be used to derive viral particles. Similarly, a cDNA copy can be made of a viral RNA genome. Alternatively, a cDNA (or viral genomic DNA) moiety can be transcribed in vitro to produce RNA. These techniques are well-known to those skilled in the art, and also are described. The transferred nucleic acid (i.e., a sequence or gene of interest) is generally linked to, e.g. inserted into, the vector nucleic acid molecule. A vector may include sequences that direct autonomous replication in a cell, or may include sequences sufficient to allow integration into host cell DNA. The vector is not a wild-type strain of a virus, inasmuch as it comprises human-made mutations or modifications. Thus, the vector typically is derived from a wild-type viral strain by genetic manipulation (e.g., by addition, deletion, mutation, insertion or other techniques known in the art) to comprise lentiviral vectors, as further described herein. Useful vectors include, for example, plasmids (typically DNA plasmids, but RNA plasmids are also of use), phages, cosmids, and viral vectors.

The term "viral vector" refers to a vector that comprises a viral nucleic acid and can also include a viral capsid and/or replication functions. As will be evident to one of skill in the art, the term "viral vector" is widely used to refer to either a nucleic acid molecule (e.g., a plasmid) that includes virus-derived nucleic acid elements that typically facilitate transfer of the nucleic acid molecule or integration into the genome of a cell or to a viral particle that mediates nucleic acid transfer. Viral particles will typically include various viral components and sometimes also host cell components in addition to nucleic acid(s).

Embodiments described herein relate to a phenotypic assay for determining HIV-1 co-receptor tropism in an HIV-1 infected patient, methods for predicting a patient's response to an HIV-1 treatment, and methods of treating HIV-1 in a subject. We found that a yeast based cloning system can be used to introduce patient-derived HIV-1 envelope (env) fragments into an expression vector. The expression vector including the HIV-1 envelope fragments can be combined with a cell to cell fusion assay to provide a highly sensitive, quick, efficient and reproducible method of determining HIV-1 tropism in as little as 0.3% of a cell population.

In some embodiments, the method can be used for determining HIV-1 co-receptor tropism in an HIV-1 infected patient. The method includes the step of preparing an HIV-1 envelope protein coding sequence from a sample obtained from the patient.

Any HIV-1 envelope protein coding sequence derived from an HIV-1 virus of a patient that mediates membrane fusion can be used. As used herein, the term "HIV-1 envelope protein" refers to a full-length protein, fragment, analog, or derivative thereof that binds to a complementary CD4 receptor and one or more co-receptors (e.g., CCR5 or CXCR4) to mediate cell fusion. The HIV-1 envelope protein derived from an HIV-1 virus of a patient may be a surface glycoprotein.

HIV-1 envelope protein coding sequences useful in the present method can include, but are not limited to HIV-1 envelope protein coding sequences encoding surface proteins from a number of different HIV-1 groups. Exemplary HIV-1 groups include both the "major" group (i.e., the M group) and the minor groups 0, N and P. An HIV-1 envelope protein useful in the present method can also include subgroups, or clades, of HIV-1 groups known in the art.

In some embodiments, the HIV-1 envelope protein coding sequences encode surface proteins from a patient infected with a HIV-1 group M subtype B variant. Non-limiting examples of subtype B HIV-1 variants can include HIV-1B-92BR014, HIV-1B-92TH593, HIV-1B-92US727, and HIV-1B-92US076.

In some embodiments, the HIV-1 envelope protein coding sequences encode surface proteins from a patient infected with a HIV-1 group M non-subtype B variant. Non-B HIV-1 group M variants can include the clades or subtypes A, C, D, F, G, H, J, K, N and circulating recombinant forms derived from recombination between viruses of different subtypes. Non-limiting examples of non-B HIV-1 subtypes include three subtype A (HIV-1A-93RW024, HIV-1A-92UG031, and HIV-1A-92UG029), four subtype C (HIV-1C-96USNG58, HIV-1C-93MW959, HIV-1C-98IN022, and HIV-1C-92BR025), five subtype D (HIV-1D-92UG021, HIV-1D-92UG024, HIV-1D-94UG114, HIV-1D-92UG038, and HIV-1D-93UG065), two subtype F (HIV-1F-93BR20 and HIV-1F-93BR29), two subtype G (HIV-1G-RU132 and HIV-1G-RU570), and six circulating recombinant forms (HIV-1AE-CMU02, HIV-1AE-CMU06, HIV-1AE-92TH021, HIV-1AE-93TH051, HIV-1AE-95TH001, and HIV-1BF-93BR029).

Samples obtained from a patient for the determination of phenotypic HIV-1 tropism can be obtained, for example, during routine patient monitoring. Samples obtained from a subject can include blood samples. In certain embodiments, the sample is a plasma sample. In some embodiments, a blood sample can be collected from a patient and plasma samples can be processed for immediate use. Alternatively, a processed plasma sample can be stored at −80° C. for analysis at a later time.

In some embodiments, a blood sample from the HIV-infected patient has a viral load ranging from about <50 to about 10,000 copies of viral RNA/ml. In some embodiments, the viral load can range from about 1000 to about 10,000 copies/ml. In certain embodiments, a blood sample from the HIV-infected patient has a viral load greater than or equal to 1,000 copies/ml.

In some embodiments, plasma viral HIV-1 RNA can be purified from pelleted virus particles using known methods. In one example, plasma viral HIV-1 RNA can be purified from pelleted virus particles by centrifuging one milliliter of a patient's plasma at 20,000 g×60 min at 4° C. using a QIAamp Viral RNA Mini Kit (Qiagen).

Once the plasma HIV-1 RNA is purified it can be reverse transcribed into HIV-1 cDNA. A representative protocol for the preparation of HIV-1 cDNA from purified HIV-1 RNA is described in the Example section where 10 μl of the backward (BWD) primer EXT TAT REC CON BWD 13 having SEQ ID NO: 47 is added to 7.25 μl of DEPC-treated $H_2O$, 2.0 μl of RT Buffer 10× and 2.0 μl of 10 mM dNTP mix. This mixture is further added to 5 μl of purified HIV-1 RNA and 4 μl of PCR water and incubated at 88° C. for 1 minute, 65° C. for 10 minutes, and then 25° C. for 5 min. The resulting mixture is then kept at room temperature. Next, 2.0 μl of 100 mM DTT, 0.25 μl (10 U) RNase inhibitor, and 0.5 μl AccuScript High-Fidelity Reverse Transcriptase (AccuRT) (STRATAGENE) is added individually to the mixture. The mixture is then incubated at 42° C. for 90 min, heat inactivated at 700 for 15 minutes, and chilled and held at 40 for PCR amplification. Alternatively, the mixture can be frozen at −20° for later amplification.

Additional backward primers for the preparation of HIV-1 cDNA from purified HIV-1 RNA are disclosed in Table below.

TABLE 1

Oligonucleotide backward (BWD) primers for the preparation of HIV-1 cDNA from purified HIV-1 RNA derived from a patient in Table 4.

| Primer Name | Location | Sequence |
|---|---|---|
| EXT TAT REC CON BWD 11 | 8699→8748 | SEQ. ID. NO. 1 |
| EXT TAT REC CON BWD 12 | 8640→8689 | SEQ. ID. NO. 2 |
| EXT TAT REC CON BWD 13 | 8562→8611 | SEQ. ID. NO. 3 |

A portion of the HIV-1 cDNA corresponding to an HIV-1 envelope protein coding sequence derived from the patient can be amplified using a PCR assay where the patient derived HIV-1 cDNA acts as a template. A representative protocol for amplifying HIV-1 cDNA from purified HIV-1 RNA is described in the Example section. In some embodiments, PCR amplification of the envelope protein coding sequence amplifies a portion of the patient's env gene from gp120 up to Tat exon 2. In some embodiments, PCR amplification of the envelope protein coding sequence amplifies a 2302 nt fragment of the HIV-1 env gene, including the entire surface glycoprotein (gp120) and most of the transmembrane glycoprotein (gp41).

The use of both external and nested env gene specific primers (i.e., a nested PCR) can be employed to amplify an HIV-1 envelope protein coding sequence of patient derived HIV-1 cDNA. In an exemplary embodiment, the external forward primer TAT REC CON FWD 3 having SEQ ID NO: 7 and the external backward primer TAT REC CON BWD 6 having SEQ ID NO: 5 can be employed in combination with the nested forward primer IntF gp120.3 having SEQ ID NO: 12 and the nested backward primer TAT REC CON BWD 4 having SEQ ID NO: 10 for the amplification of a 2,302 nt fragment including all the surface glycoprotein (gp120) and most of the transmembrane glycoprotein (gp41) coding sequence of the patient's envgene, missing only 321 nt of the gp41 cytoplasmic domain.

Additional external and nested env gene specific primers for amplifying a portion of the HIV-1 cDNA corresponding to an HIV-1 envelope protein coding sequence derived from a patient are disclosed in Table 2 below.

TABLE 2

Oligonucleotide forward (FWD) and backward (BWD) external primers and nested primers for the insertion of HIV-1 envelope protein coding sequence derived from a patient into pREC nfl HIV-1 envΔ/URA3 vectors to create patient derived pREC nfl HIV-1 vectors

| | | |
|---|---|---|
| TAT REC CON FWD 1 | 5758→5808 | SEQ. ID. NO. 9 |
| TAT REC CON FWD 2 | 5732→5782 | SEQ. ID. NO. 4 |
| TAT REC CON FWD 3 | 5713→5762 | SEQ. ID. NO. 7 |
| TAT REC CON BWD 4 | 8425→8474 | SEQ. ID. NO. 10 |
| TAT REC CON BWD 5 | 8429→8478 | SEQ. ID. NO. 11 |
| TAT REC CON BWD 6 | 8439→8488 | SEQ. ID. NO. 5 |
| TAT REC CON BWD 7 | 8493→8542 | SEQ. ID. NO. 14 |
| Int Fwd gp120.3 | 6179→6198 | SEQ. ID. NO. 12 |

Amplified PCR products corresponding to a patient derived HIV-1 envelope protein coding sequence (i.e., the patient derived env amplicon) can then be purified for use in the next step of the method. For example, PCR cDNA products corresponding to the gp120/gp41-coding regions of an HIV-1 envelope protein derived from a patient can be purified using a QIAquick PCR Purification Kit (QIAGEN).

The patient derived HIV-1 envelope protein coding sequence is then introduced into a first expression construct using a yeast based homologous recombination/gap repair method. An expression construct can include a vector, such as a plasmid. A suitable vector includes at least one origin of replication, a region of the DNA that is substantially identical to the primer binding site (pbs) of HIV-1, a selectable gene replacing at least a portion of the env gene of HIV-1, and a region of DNA that is substantially identical to the 3' end of the long terminal repeat region of HIV. By "substantially identical", it is meant that the regions have sufficient homology with the named segments of DNA as to be able to hybridize under stringent conditions.

The vector can also comprise a partial retrovirus genome, specifically; the vector can include a near full length (NFL) HIV-1 genome devoid of the 5' LTR. Lack of a 5' LTR allows the HIV-1 genome to be located precisely in front of the CMV promoter in the vector such that transcription would be initiated at the first nucleotide of the primer binding site. Cloning the HIV-1 sequence in this way could not be performed with restriction enzymes but can be performed by yeast recombination. In addition a vector devoid of the HIV-1 5' LTR is unable to produce infectious virus.

In some embodiments, the vectors can include a sequence corresponding to a near full length HIV-1 backbone. The near full length HIV-1 backbone can include a HIV-1 Group M subtype B backbone (e.g., HIV-1$_{NL4-3}$). In certain embodiments, the vector can recombine with not only homologous env protein coding sequences derived from patients infected with Group M subtype B wild-type and multidrug resistant strains of HIV-1 but also from sequences derived from patients infected with other non-B HIV-1 group M subtypes. Therefore, in some embodiments the near full length HIV-1 backbone of a vector can include a minor HIV-1 group backbone and the method described herein can be used to determine HIV-1 co-receptor tropism in a patient infected with a minor HIV-1 group strain. Exemplary minor HIV-1 group backbones can include Group N, Group O and Group P strains near full length HIV-1 backbones.

In certain embodiments, the near full length HIV-1 yeast-based vector pREC nfl HIV-1 Δenv/URA3 can be used. pREC nfl HIV-1 Δenv/URA3 contains the selection marker URA3. URA3 encodes the orotidine-5'-phosphate decarboxylase protein involved in the bio-synthesis of uracil. To prepare pREC nfl HIV-1 Δenv/URA3, URA3 is recombined in yeast to replace a section of the env gene in the pREC nfl HIV-1 vector (SEQ ID NO: 13) resulting in a vector having the pREC nfl HIV-1 sequence except with a URA3 gene inserted into and replacing a portion of the envelope gene. Successful recombinants may be selected by growing the yeast transformed with the URA3 and the pREC nfl HIV-1 on uracil-deficient media. In certain embodiments, at least a portion of the 5' and 3' ends of the pREC nfl HIV-1 env gene remain so as to permit further recombination.

In addition to URA3, a pREC nfl HIV-1 Δenv/URA3 vector can also include a yeast transformation selection marker gene that does not replace a portion of the envelope gene (e.g., LEU2 or TRP1).

Expression constructs can be made, for example, by replacing various portions of the HIV-1 env gene in the pREC nfl HIV-1 vector with a selectable marker such as URA3. URA3 may be inserted into the pREC nfl HIV-1 vector at different sites for replacement of the gp120/gp41, the gp120, or V3 coding sequence in the HIV-1 envelope gene, for example. A list of near full length HIV-1 isolates containing a URA3 substitution for use herein is provided in Table 3.

TABLE 3 pREC nfl HIV-1 vectors with various coding region replacements with URA3

| pREC-$_{NFL-HIV-1}$ Deletions | Location of Deletion in NL4-3 | Size of Deletion |
|---|---|---|
| Δenv\URA3 | 6221-8785 | 2565 |
| Δenv-s\URA3 | 6221-8264 | 2043 |
| Δenv gp120\URA3 | 6221-7747 | 1527 |
| Δenv gp120 v1/v2\URA3 | 6611-6802 | 192 |
| Δenv gp120 v3\URA3 | 7100-7207 | 108 |
| Δenv gp120 v4/v5\URA3 | 7368-7627 | 260 |
| Δenv gp41\URA3 | 7748-8785 | 1038 |
| Δenv gp41-s\URA3 | 7748-8264 | 517 |

To insert the purified HIV-1 envelope protein coding sequence derived from a patient and replace a selectable gene encoded by the vector, a yeast strain (e.g., Strain BY4727) may be transformed with either linearized or non-linearized pREC nfl HIV-1 Δenv/URA3 vector, using a lithium acetate technique for example, along with the purified HIV-1 envelope protein coding cDNA sequence derived from a patient. The patient derived cDNA recombines with the remaining portions of the env gene flanking the URA3 gene in pREC nfl HIV-1 Δenv/URA3. The resulting recombinants contain a near full length HIV-1 sequence from the NL4-3 HIV-1 strain, with a patient-derived env gene or gene fragment replacing the env gene of NL4-3.

In an exemplary embodiment, PCR products spanning the gp120/gp41-coding region of HIV-1 derived from a patient are introduced via yeast homologous recombination into a pRECnfl ΔEnv/URA3 vector. The pRECnfl-TRPΔEnv/URA3 vector includes a near-full length HIV-1 genome where a yeast uracil biosynthesis (URA3) gene has replaced the native gp120/gp41 HIV-1 coding sequence (FIG. 1A). Following successful yeast homologous recombination of the gp120/gp41-coding region of HIV-1 derived from a patient and the pRECnfl-TRPΔEnv/URA3 vector, the vector construction expresses all HIV-1 coding regions, that is, all genes corresponding to the HIV-1$_{NFL4-3}$ strain used as backbone in the vector plus the patient-derived HIV-1 envelope protein coding sequence; however, it is unable to produce infectious virus since it is missing the 5' LTR region.

Yeast colonies containing a recombined sequence in the pREC nfl HIV-1 vectors, for example, where a URA3 gene has been replaced by the HIV-1 envelope protein coding sequence derived from a patient, may be selected on plates containing a selection agent, such as CMM-Leu+5-Fluoro-1,2,3,6-Tetrahydro-2,6-Dioxo-4-Pyrimidine Carboxylic Acid (FOA). FOA is converted to the toxic substrate 5-fluorouracil by the URA3 gene product, orotidine-5'-phosphate decarboxylase. FOA-resistant yeast including the newly recombined expression construct can then be grown in yeast complete minimal medium.

Organisms other than yeast may also be utilized to provide homologous recombination. For example, the bacterial strains TB10-pyrF287 and TB10ΔpyrF can also be used for recombination of patient derived HIV-1 envelope protein sequences into the pREC nfl HIV-1 plasmids. TB10ΔpyrF strain genotype is nad::Tn10/pλ-Δcro-bro tetr pyrF. TB10ΔpyrF287 strain genotype is nad::Tn10/pk-Δcro-bro tetr pyrF287. These strains express X bet, gam, and exo for hyper-recombination. Additionally, pyrF is the homolog to URA3. Deleting and mutating pyrF in TB10-pyrF287 and TB10pyrF can allow URA3 plasmids to be used for selection. This will allow the same plasmids to be currently used in the yeast system to be used in the bacterial system.

Following homologous recombination, the first expression construct can then be extracted and purified from the organism providing recombination. For example, recombined pREC nfl HIV-1 vectors including the HIV-1 envelope protein coding sequence derived from a patient can be purified from the entire number of yeast colonies. In some embodiments, the first expression construct is extracted and purified from about 200 to greater than 1000 individual yeast colonies.

The purified expression construct can then be transformed into bacteria (e.g., E. coli) for plasmid vector propagation. In an exemplary embodiment, Electrocomp TOP10 E. coli bacteria cells (Invitrogen) can be transformed with purified recombined pREC nfl HIV-1 vectors. Plasmid DNA, once purified from the bacteria, can be stored at −80C until further use. In an alternative embodiment, bacterial colonies can be transformed with crude yeast extract without the purification step. In some embodiments, transformed bacterial colonies can be screened for the env insert and absence of the URA3 gene using well known methods.

A first cell can then be transfected with the first expression construct and a second expression construct, which includes a first reporter molecule fragment coding sequence, so that the patient-derived HIV-1 envelope protein and the first reporter molecule fragment are expressed on a surface of the first cell.

Methods of transfecting and expressing genes in mammalian cells are known in the art. Transducing cells with viral vectors can involve, for example, incubating vectors with cells within the viral host range under conditions and concentrations necessary to cause transduction. See, e.g., Methods in Enzymology, vol. 185, Academic Press, Inc., San Diego, Calif. (D. V. Goeddel, ed.) (1990) or M. Krieger, Gene Transfer and Expression—A Laboratory Manual, Stockton Press, New York, N.Y.; and Muzyczka (1992) Curr. Top. Microbiol. Immunol. 158: 97-129, and references cited in each. The culture of cells, including cell lines and cultured cells from tissue samples is well known in the art. Freshney (Culture of Animal Cells, a Manual of Basic Technique, Third edition Wiley-Liss, New York (1994)) provides a general guide to the culture of cells.

The second expression construct can include a vector, such as a plasmid. Suitable vectors for use in eukaryotic and prokaryotic cells are known in the art and are commercially available or readily prepared by a skilled artisan. Additional vectors can also be found, for example, in CURRENT PROTOCOLS IN MOLECULAR BIOLOGY (Ausubel, F. M., et al., eds. 2000) and Sambrook et al., "Molecular Cloning: A Laboratory Manual," 2nd ED. (1989), the teachings of which are incorporated herein by reference. In some embodiments, transformation of a cell with a reporter molecule fragment sequence can be achieved using calcium phosphate, DEAE-dextran, electroporation, cationic lipid reagents, or any other convenient technique known in the art.

In some embodiments, the second expression vector is a mammalian expression vector including a promoter operably linked to a reporter molecule fragment expression sequence. For example, a CMV promoter-based vector can be used. Human cytomegalovirus (CMV) promoter regulatory region drives constitutive protein expression.

The first reporter molecule fragment can be one portion of reporter molecule capable of alpha complementation. In alpha complementation, a reporter molecule is a molecule whose activity is lost if the essential portions or subunits are separated, and whose activity is restored when the portions are expressed in proximity to one another. The activity can be enzymatic, catalytic, and the like, where such activity can be measured in at least a semi-quantitative fashion. Enzymes known to reform from peptide fragments and regain enzymatic activity include, but are not limited to ribonuclease (Richards, et al., J. Biol. Chem. 234: 1459 (1959)), staphylcoccal nuclease (Light, et al., J. Biol. Chem. 249: 2285 (1974)), and β-galactosidase (Langley and Zabin, Biochemistry 15: 4866 (1976)).

In one embodiment, the reporter molecule is β-galactosidase (or β-gal) and the first reporter molecule fragment is the α-fragment of β-gal. β-gal is a tetrameric protein having a molecular weight (MW) equal to 540,000 daltons. The four identical monomers consist of 1021 amino acids, each with a MW of 116,000 daltons. The monomeric protein is divided into three regions; (1) the N-terminal proximal segment (the α-region), (2) a middle region, and (3) a C-terminal distal segment (the co-region). The amino-terminal domain of the protein, otherwise known as the α-domain, is about 100 amino acids and mediates tetramerization. The carboxyterminal domain, otherwise known as the ω-domain, contains the active site of the enzyme. When individually expressed as separated domains, the α-domain and ω-domain are enzymatically inactive. However, when the two fragments are present in a single cell, they re-associate to form an active enzyme, a phenomenon termed α-complementation.

In an exemplary embodiment, the second expression construct includes the CMV promoter-based vector, pCMVα, wherein the CMV promoter is operably linked to an α-fragment of β-gal expression sequence.

The first cell as provided herein expresses the patient-derived HIV-1 envelope protein and the first reporter molecule fragment. Therefore, the first cell, or "donor cell", represents the HIV-1 virus particle or HIV-1 virally-infected cell of a patient whose HIV-1 co-receptor tropism is being determined.

Any cell can be used a the first cell. The cell can be human or nonhuman. The cell can be freshly isolated (i.e., primary) or derived from a short term- or long term-established cell line. In one embodiment, the first cell is a eukaryotic cell, where the eukaryotic cell is a cell that can be grown in culture, using standard laboratory procedures and media well known to those of skill in the art.

In some embodiments, the first cell can be any cell that is not susceptible to toxic effects of chronically expressing viral envelope proteins, that permit cell surface expression of such proteins, and that does not express endogenous proteins that inhibit cell fusion. The first cell can also be a cell that does not express complete complementary cell surface receptors or co-receptors for the expressed patient-derived HIV-1 envelope protein and therefore will not undergo fusion with itself.

Examples of biological cell lines include NIH-3T3 murine fibroblasts, quail QT6 cells, canine Cf2Th thymocytes, Mv1 Lu mink lung cells, Sf9 insect cells, primary T-cells, human T-cell lines (e.g., H-9), U-87 MG glioma, SCL1 squamous cell carcinoma cells, CEM, HeLa epithelial carcinoma, Chinese hamster ovary (CHO) cell, SF33 cell and HEK293T cell. Such cell lines are described, for example, in the Cell Line Catalog of the American Type Culture Collection (ATCC, Rockville, Md.). In one embodiment, the first cell is a HeLa epithelial carcinoma cell or a human HEK293T cell.

The first cell can express the patient-derived HIV-1 envelope protein necessary for cell fusion and a first reporter molecule fragment exogenously (e.g., as a result of the stable transfer of genes). Exogenous expression by a cell as provided herein can result from the introduction of the first and second expression constructs having nucleic acid sequences encoding a patient derived HIV-1 viral envelope protein and first reporter molecule fragment, respectively.

Exogenous expression of the patient derived HIV-1 envelope protein and reporter molecule fragment can be transient, stable, or some combination thereof. Exogenous expression can be enhanced or maximized by co-expression with one or more additional proteins, e.g., HIV rev. Exogenous expression can be achieved using expression constructs including constitutive promoters, e.g., SV40, CMV, and the like, and inducible promoters known in the art. Suitable promoters are those, which will function in the donor cell of interest.

In one embodiment, a first cell stably expresses the patient-derived HIV-1 envelope protein and displays it on the cell surface. For example, a first cell may comprise a coding sequence for the patient-derived HIV-1 envelope protein stably integrated into its genome in a manner such that it is expressed in the first cell and directed to the cell surface where it is displayed in a functional manner. The first cell can include a first expression construct made up of a suitable promoter operably linked to the patient-derived HIV viral envelope protein encoding sequence, where the expression construct is integrated into the first cell genome in a manner such that the envelope coding sequence is expressed in the cell and the expressed viral envelope protein is transported to the cell surface where it is displayed in a functional manner. In a specific embodiment, the patient-derived HIV-1 envelope protein includes all of HIV-1 gp120 and most of HIV-1 gp41.

A second cell is also provided that expresses on the cell surface a second reporter molecule fragment complementary to the first reporter molecule fragment, an HIV-1 envelope protein receptor (e.g., CD4) and an HIV-1 envelope protein co-receptor that can be potentially capable of binding to the patient-derived HIV-1 viral envelope protein expressed on the surface of the first cell. The second represents the target cell, i.e., the cell that the virus of interest enters.

In one embodiment, the second cell is a eukaryotic cell that can be grown in culture, using standard laboratory procedures and mediums well known to those of skill in the art. The second cell may be any cell that can stably express the complete viral envelope protein receptor and co-receptor as well as a second reporter molecule fragment without toxic effects and that does not express endogenous proteins that inhibit cell fusion. The HIV-1 envelope protein receptor and its co-receptor are expressed on the surface of the second cell and are the cell surface receptor proteins that may be employed by the HIV-1 env protein derived from a given patient for receptor mediated fusion entry.

In some embodiments, the second cell stably expresses the HIV-1 viral envelope protein receptor, CD4, and co-receptor (CCR5 and/or CXCR4), and displays them on the surface of the second cell. Therefore, the second cell may comprise a coding sequence for the HIV-1 envelope protein receptor and co-receptor stably integrated into its genome in a manner such that they are expressed in the second cell and directed to the cell surface where they are displayed in a functional manner.

In some embodiments, the second cell can be transfected with an expression construct made up of a suitable promoter operably linked to the HIV-1 envelope protein receptor-encoding sequence, where the expression construct is integrated into the second cell genome in a manner such that the viral envelope protein receptor-encoding sequence is expressed and the expressed viral envelope protein receptor is transported to the cell surface where it is displayed in a functional manner.

The second cell can be prepared using standard molecular biology procedures. In some embodiments, the second cell is a stable cell line, such as a U87 cell, 293T cell, SF33 cell, HeLa cell, or the like. A method of making a second cell expressing on the cell surface an HIV-1 envelope protein receptor and an HIV-1 envelope protein co-receptor can include contacting a cell with an expression construct containing a suitable promoter operably linked to an HIV viral envelope protein receptor coding sequence; contacting the cell with another expression construct containing a suitable promoter operably linked to an HIV viral envelope protein co-receptor coding sequence, whereby the HIV viral envelope protein receptor and co-receptor are expressed in a functional form on the cell surface.

The HIV viral envelope protein receptor, or its co-receptor can also include fragments of the receptor or co-receptor. As used herein, the term "fragment" refers to any biologically active fragment of the proteins described herein. Such fragments can include a portion of the full-length sequence of the protein and yet possess the same function, possibly to a greater or lesser extent. For example, fragments comprising deletion mutants of an HIV viral envelope protein receptor or HIV viral envelope protein co-receptor can be designed and expressed by well known laboratory methods. Such fragments can be evaluated for fusogenic properties routinely using the assays provided herein as an indicator of biological activity.

Likewise, any analog or derivative of the viral envelope protein receptor or its co-receptor can be used in the methods herein. As used herein, the term "analog or derivative" refers to substituted proteins characterized by the ability to bind a viral envelope protein receptor (or co-receptor) as indicated. Such mutations and substitutions can be designed and expressed by well-known laboratory methods. Such fragments can be evaluated for fusogenic properties routinely using the assays provided herein as an indicator of biological activity. Furthermore, any combination of biologically functional molecules may be used to mediate the cell fusion event. Biologically functional molecules can include full-length proteins, fragments, analogs, or derivatives thereof. Such biologically functional molecules can multimerize for activity or be active in monomer form.

The level of expression of the HIV-1 envelope protein receptor and co-receptor is the level required to mediate the cell fusion event. One of ordinary skill in the art can determine the required level of expression for fusogenic activity using assays routinely employed in the art.

In some embodiments, the second cell can be contacted with a third expression construct containing a suitable promoter operably linked to a second reporter molecule fragment coding sequence that is expressed on the surface of the second cell. In one embodiment, an HIV-1 envelope protein receptor and its co-receptor are encoded in a different vector or plasmid than the second reporter molecule fragment. In another embodiment, the HIV-1 envelope protein receptor and its co-receptor are encoded in the same vector or plasmid as the second reporter molecule fragment.

Alternatively, in some embodiments, the second cell can be a $CD4^+$ cell line stably expressing a co-receptor at the cell surface (e.g., U87.CD4.CCR5 or U87.CD4.CXCR4). Target second cells can also include cell lines that naturally express $CD4^+$ and CCR5 and/or CXCR4. In the case of a cell line stably expressing both CCR5 and CXCR4, either CCR5 or CXCR4 expression can be knocked down.

The second reporter molecule fragment can include the complementary domain to the first reporter molecule fragment such that the two fragments are capable of alpha complementation. In some embodiments, the reporter molecule is β-galactosidase and the second reporter molecule fragment is the ω-fragment of β-gal. In an exemplary embodiment, the second expression construct includes the CMV promoter-based vector, pCMVω, wherein the CMV promoter is operably linked to a ω-fragment of β-gal expression sequence.

Once a nucleic acid is incorporated into the first or second cell as provided herein, the cells can be maintained under suitable conditions for expression of the exogenous patient-derived HIV viral envelope protein and first reporter molecule segment (i.e., the first cell), or HIV-1 envelope protein receptor, its co-receptor, and the second reporter molecule fragment (i.e., the second cell). Generally, the cells are maintained in a suitable buffer and/or growth medium or nutrient source for growth of the cells and expression of the gene product(s). Exemplary growth medium can include, but is not limited to, DMEM medium/L-glutamine (GIBCO; CELLGRO; MEDIATECH) supplemented with FBS (CELLGRO), penicillin/streptomycin (GIBCO), puromycin and G418 (MEDIATECH).

The second cell can then be contacted with the first cell to determine if the first cell fuses with or to the second cell. An HIV-1 envelope protein derived from a subject can expressed by the first cell (i.e., the donor cell) can bind to complementary HIV-1 envelope protein receptor (e.g., CD4) and one or more co-receptors (e.g., CCR5 or CXCR4) expressed on the second cell (i.e., the target cell) to mediate fusion of the membranes of the two cells. The binding of the HIV-1 envelope protein to its complementary receptor and co-receptor initiates the fusogenic process that subsequently results in fusion of the two cells into one hybrid cell.

In some embodiments, the methods provided herein permit a quantitation of fusogenic activity between cells that express the complementary patient-derived HIV-1 envelope protein and receptor and co-receptors exogenously. Such cells further express the complementary first reporter molecule fragment and the second reporter molecule fragment. In other embodiments, the methods provided herein are useful in identifying the HIV-1 co-receptor tropism (e.g., CCR5 or CXCR4) of the patient-derived HIV-1 envelope protein by screening for fusogenic activity between the first cell, the first cell exogenously expressing a patient-derived HIV-1 envelope protein and a first reporter molecule fragment, and a second cell that exogenously expresses CD4, a particular HIV co-receptor (e.g., CCR5 or CXCR4), and a second reporter molecule fragment.

The first cell and second cell or a plurality of first cells and second cells can be contacted using any convenient protocol. In one embodiment, the first cell and second cell can placed into a container that can hold a volume of a fluid medium, e.g., a well of a 96-well plate or 384 well plate, or an analogous structure. The first and second cells can be contacted in any volume with any cell number that will permit accurate detection of cell fusion events. In one embodiment, the total number of cells present ranges from about 1,000 to about 100,000 cells. In one embodiment, the reaction volume ranges from about 20 to about 200 microliters.

The cells can be contacted for any period of time. For example, the cells can be mixed and incubated for an amount of time suitable for the patient-derived HIV-1 envelope protein expressed on the surface of a first cell to bind to the CD4/co-receptor complex expressed on the surface of a second cell. In one embodiment, the time of contact ranges from one hour to eight hours, with a preferred time of four hours. The first and second cells can be contacted in medium at any pH that is permissive for cell fusion. The first and second cells can be contacted at various temperatures. In one embodiment, the temperature for contact of the first and second cells often ranges from 25° C. to 38° C., with a temperature of 37° C. typically utilized. When desirable, the first and second cells may be agitated to ensure adequate mixing and presentation of viral envelope protein to its receptor.

The presence or absence of cell fusion is determined by the detection of the presence or absence of a signal produced by a functional reporter molecule, whereby the presence of cell fusion is detected by the presence of a signal and the absence of cell fusion is detected by the absence of signal. The functional reporter molecule is formed when the first reporter molecule fragment and the second reporter molecule fragment combine. The particular detection protocol employed necessarily varies depending on the nature of the detectable product. For example, where the detectable product is a fluorescent protein, the lysate can be irradiated with light of an appropriate wavelength to excite the fluorescent protein and emission from the fluorescent protein is detected.

In one embodiment, the functional reporter molecule is an enzyme whose activity can be monitored by the appearance of a product of the enzymatically catalyzed reaction or by disappearance of the enzyme substrate. In another embodiment, the functional reporter molecule can be detected without addition of exogenous substrate by measurement of some endogenous property (e.g., luminescence, chemiluminescence).

In embodiments where the functional reporter molecule is an enzyme that converts a substrate to a detectable product, the detection can require contacting the cell lysate with a substrate for the reporter enzyme. The substrate may be contacted with the lysate using any convenient protocol, e.g., by placing the lysate into a container having the substrate, by introducing the substrate into the lysate, etc. The nature of the particular substrate necessarily depends on the nature of the reporter enzyme, which is present in the two fragments. For example, the substrate can be one that is converted by the reporter enzyme into a chromogenic product. Of interest in certain embodiments are substrates that are converted by the enzyme into a fluorescent product. The amount of substrate that is contacted with the lysate may vary, but typically ranges from about 1 femtomolar to 10 millimolar.

Representative substrates that can be used for spectrophotometric or fluorometric analysis include, but are not limited to: p-aminophenyl-β-D-galactopyranoside; 2'-N-(hexadecanol)-N-(amino-4'-nitrophenyl)-β-D-galactopyranoside; 4-methylumbel-liferyl-β-D-galactopyranoside; napthyl-AS-B1-β-D-galactopyranoside; 1-napthyl-β-D-galactopyranoside; 2-napthyl-β-D-galactopyranoside monohydrate; O-nitrophenyl-β-D-galactopyranoside; m-nitrophenyl-β-D-galactopyranoside; p-nitrophenyl-β-D-galactopyranoside; and phenyl-β-D-galactopyranoside, 5-bromo-4-chloro-3-indolyl-β-D-galactopynanoside, resorufin-β-D-galactopyranoside, 7-hydroxy-4-trifluoromethyl coumarin, Ω-nitrostyryl-β-D-galactopyranoside, and flourescein-β-D-galactopyranoside.

The substrate conversion can be evaluated in whole cells or in lysate depending on the nature of the substrate and the final detectable product as is known in the art.

In one embodiment, the lysate is evaluated for the presence or absence of detectable product following a predetermined incubation period, where this incubation period typically ranges from about 1 minute to about 2 hours. The particular detection protocol employed varies depending on the nature of the detectable product. For example, where the detectable product is a fluorescent product, the detection protocol employs the use of a fluorescent light detection means, e.g., a fluorescent light scanner, which can scan the lysate for the presence of fluorescent signal. The presence or absence of detectable signal from the signal producing system, e.g., detectable product in the lysate, is then used to derive information as to whether cell fusion occurred. The presence of a signal in the lysate is indicative of cell fusion.

The signal generated by the functional reporter molecule can be correlated to the cell fusion event in a qualitative or quantitative manner. One also can employ a threshold value, whereby any signal above the threshold value represents sufficient activity and any signal below the threshold value represents insufficient activity. One also can evaluate the signal in a quantitative or a semi-quantitative manner, in which the amount of signal detected is used as a direct indication of the level of cell fusion events mediated by either a CCR5 or CXCR4 co-receptor. The amount of signal detected may be linear or non-linear relative to the amount of cell fusion depending on the sensitivity of the reporter molecule and substrate employed. In one embodiment, a larger amount of signal indicates a greater amount of cell fusion, such that the amount of signal has a direct relationship with the amount of cell fusion.

The above signal evaluation may be accomplished using any convenient means. Thus, the signal may be subjectively evaluated by comparing the signal to a set of control signals. The evaluation may be done manually or using a computing or data processing means that compares the detected signal with a set of control values to automatically provide a value for the cell fusion activity. In some embodiments, quantified interactions can be expressed in terms of relative light units.

In an exemplary embodiment, 2 μg of an HIV-1 expression vector carrying the patient-derived env gene, and 2 μg of the pCMVα vector expressing the α-fragment of the β-galactosidase gene are co-transfected into $7 \times 10^6$ HEK293T donor cells using Lipofectamine 2000 (Invitrogen). Target cells expressing CD4 and a co-receptor (U87.CD4.CCR5 and U87.CD4.CXCR4) are transfected with 4 μg of the pCMVω vector expressing the ω fragment of the β-galactosidase gene. 48 hours post-transfection the donor and target cells are washed three times with 1×PBS, removed from the cell-culture plates using 1× solution of PBS and 3 mM EDTA, counted and re-suspended in DMEM at a concentration of $2 \times 10^6$ cell per milliliter. Fifty microliters (~$1 \times 10^5$ cells) of donor and target cells are mixed and added together into 96 well plate and incubated for 4 hours at 37° C. in 5% $CO_2$. Cell-to-cell fusion events are quantified by measuring luminescence related to β-galactosidase activity (relative light units, RLU) using the Galacto-star system (Applied Biosciences, Bedford, Mass.) in a multi-well plate reader.

In particular embodiments, the presence of a signal generated by the reporter molecule upon a fusion event is indicative of the HIV-1 co-receptor tropism in the HIV-infected subject. The quantity of signal generated can be indicative of the relative cell fusion between donor cells and target cells expressing either the CCR5 or CXCR4 CD4 co-receptor. Therefore, the signal generated (e.g., β-galactosidase activity) can indicate the HIV-1 co-receptor tropism of the patient. For example, fusion of a donor cell and a target cell expressing CXCR4 can produce a level of β-galactosidase activity indicative of the patient being infected with CXCR4-tropic (non-CCR5) viruses. Likewise, fusion of a donor cell and a target cell expressing CCR5 can produce a level of signal indicative of the patient being infected with CCR5-tropic viruses.

A patient may also be infected with both CXCR4-tropic and CCR5-tropic viruses simultaneously. In this case, the signal measured when mixing donor cells and target cells expressing CCR5 and CXCR4 co-receptors can be compared to control activity levels in order to determine the percentage of CCR5-tropic and CXCR4-tropic viruses in the patient.

In some embodiments, a control activity level can include the amount of activity generated by donor cells transfected with pCMV-β-gal, a vector expressing the full-length functional enzyme. Cells transfected with a and co expression vectors alone contain very low β-galactosidase activity. In contrast, when the two vectors are cotransfected, they complement to yield highly active enzyme where the α-complemented enzyme is nearly as active as the native enzyme, resulting in β-galactosidase activity more than 1000-fold above background levels. Therefore, in an exemplary embodiment, the amount of β-galactosidase activity detected when mixing donor cells and target cells having CXCR4 co-receptors can be compared to the relative light units (RLUs) generated by donor cells transfected with pCMV-β-gal to determine the percentage of CXCR4-tropic viruses in the patient.

Given their mechanism of action, the effectiveness of a CCR5 antagonist treatment in a given patient can be correlated with the amount or presence of minority non-CCR5 viruses (e.g., CXCR4) within the HIV-1 population of a patient. Therefore, in another aspect of the application, a method of predicting a patient's response to a treatment can include determining HIV-1 co-receptor tropism in an HIV-infected patient as described herein. The method further includes predicting the patient's response to the treatment based on the presence or absence of a signal generated from functional reporter molecules. For example, absence of a detectable signal generated by the fusion of a donor cell expressing an HIV-1 envelope protein derived from the patient and a target cell expressing CXCR4 can be indicative of the patient not being infected with CXCR4-tropic viruses and therefore further indicative that the patient is likely to have a positive response to CCR5 antagonist treatment.

Alternatively, in some embodiments, phenotypic dominance of CXCR4-tropic viruses in a patient renders CCR5 antagonists therapeutically ineffective. Thus, the presence of a detectable signal, or a predetermined amount of signal, generated by the fusion of a donor cell expressing an HIV-1 envelope protein derived from the patient and a target cell expressing CXCR4 can be indicative of the patient being infected with CXCR4-tropic viruses and therefore further indicative that the patient is not likely to have a positive response to CCR5 antagonist treatment.

In some embodiments, once the HIV-1 co-receptor tropism of the patient is determined, an appropriate anti-retroviral agent or anti-retroviral therapy can be administered to the patient. In some embodiments, a patient determined to be infected with CCR5-tropic viruses can be administered a CCR5 antagonist agent. Any CCR5 antagonist known in the art can be employed. CCR5 antagonists can include, but are not limited to maraviroc (Selzentry/Celsentri, Pfizer, NY) or a maraviroc based regimen, and the CCR5 entry inhibitor vicriviroc (Merck & Co., NJ).

In another embodiment, a patient determined to be infected with CXCR4-tropic viruses can be administered a CXCR4 antagonist agent. In some embodiments, the patient can be determined to have both CCR5-tropic and CXCR4-tropic viruses, in which case the patient can be administered a CCR5 antagonist and/or a CXCR4 antagonist agent. Any CXCR4 antagonist known in the art can be employed.

The CCR5 antagonist and/or a CXC4 antagonist may be administered to a patient by any conventional route of administration, including, but not limited to, intravenous, oral, subcutaneous, intramuscular, intradermal and parenteral administration. The CCR5 antagonist and/or a CXC4 antagonist can be provided in a pharmaceutical composition for administration to the patient. A pharmaceutical composition can include a proper vehicle for delivery of the therapeutic agent(s).

Optimal dosages to be administered may be readily determined by those skilled in the art, and will vary with the particular compound used, the strength of the preparation, the mode of administration, and the advancement of the disease condition. In addition, factors associated with the particular patient being treated, including patient age, weight, diet and time of administration, will result in the need to adjust dosages.

The compositions and methods of the application will now be described in greater detail in the following non-limiting Example.

Example 1

We have developed and characterized a phenotypic test to determine HIV-1 co-receptor tropism (VERITROP) based on a yeast-based cloning system and a sensitive cell-to-cell fusion assay. We compared this new assay with several phenotypic and genotypic tests, including deep sequencing that allows for minor variant detection, and showed that VERITROP is able to detect low levels of non-R5 viruses (0.3%) in plasma samples from HIV-infected individuals.

Materials and Methods

Cells and Viruses

U87.CD4.CCR5 and U87.CD4.CXCR4 cells were obtained through the AIDS Research and Reference Reagent Program, Division of AIDS, NIAID, NIH while the HEK293T cells were obtained from Stanford University (Stanford, Calif.). U87.CD4.CCR5 and U87.CD4.CXCR4 cells were maintained in DMEM medium with L-glutamine (Cellgro; Mediatech) supplemented with 15% fetal bovine serum, 100 U of penicillin/mL, 100 µg of streptomycin/mL, 1 µg/ml of puromycin, and 300 µg of G418 (all reagents from Mediatech). HEK293T were maintained in DMEM medium/L-glutamine (Gibco), 10% FBS (Cellgro), and penicillin/streptomycin (Gibco). The following viruses were obtained from the AIDS Research and Reference Reagent Program, Division of AIDS, NIAID, NIH: HIV-1A-93RW024, HIV-1A 92UG031, HIV-1A-92UG029, HIV-1B-HXB2, HIV-1B-92BR014, HIV-1B-92TH593, HIV-1B-92US727, HIV-1B-92US076, HIV-1C 96USNG58, HIV-1C-93MW959, HIV-1C-98IN022, HIV-1C-92BR025, HIV-1D-92UG021, HIV-1D-92UG024, HIV-1D-94UG114, HIV-1D 92UG038, HIV-1D-93UG065, HIV-1F-93BR20, HIV-1F-93BR29, HIV-1G-RU132, HIV-1G-RU570, HIV-1AE-CMU02, HIV-1AE-CMU06, HIV-1AE-92TH021, HIV-1AE-93TH051, HIV-1AE-95TH001, and HIV-1BF-93BR029. Tissue culture dose for 50% infectivity (TCID50) was determined in triplicate for each serially diluted virus using the Reed and Muench method and viral titers expressed as infectious units per milliliter (IU/ml). Aliquots of DNA and RNA viruses were obtained from Zeptometrix Corporation, Buffalo, N.Y. (BK virus, BKV; Epstein-Barr virus, EBV; Hepatitis B virus, HBV; Hepatitis C virus, HCV; Human Herpesvirus 6, HHV-6; Human T lymphotropic viruses type 1 and 2, HTLV-1 and HTLV-2; Cytomegalovirus, CMV; Herpes simplex virus 1 and 2; HSV-1 and HSV-2, and Varicella zoster virus, VZV) and Advanced Biotechnologies, Inc., Columbia, Md. (Human Herpesvirus 7, HHV-7 and Human immunodeficiency virus type 2, HIV-2).

Clinical Samples

Plasma samples for the characterization and verification of the phenotypic HIV-1 tropism assay were obtained during routine patient monitoring from a well-characterized cohort of HIV-infected individuals at the AIDS Clinical Trials Unit (ACTU) at Case Western Reserve University/University Hospitals of Cleveland (Cleveland, Ohio). A total of 76 RNA specimens, derived from plasma samples collected from HIVinfected individuals enrolled in the (i) maraviroc expanded access program in Europe or (ii) ALLEGRO trial, were obtained from the Hospital Carlos III (Madrid, Spain). Phenotypic HIV-1 co-receptor tropism was determined at baseline using the original version of the Trofile™ assay (Monogram Biosciences), which had a reported non-R5 variant detection limit of 5 to 10%. Written informed consent was obtained from the patients before participation in the study as previously described. Blood specimens from Cleveland were collected fresh and plasma samples were processed and stored at −80° C. for further analysis. RNA samples from Spain were shipped in dry-ice and stored at −80° C. until analysis.

RT-PCR Amplification and Nucleotide (Population) Sequence Analysis

Plasma viral RNA was purified from pelleted virus particles by diluting one milliliter of plasma with 400 µl of Phosphate Buffered Saline (PBS) 1× solution and centrifuging at 20,000 g×60 min at 4° C., removing 1,260 µl of cell-free supernatant and resuspending the pellet in the remaining 140 al, to finally extract viral RNA using QIAamp Viral RNA Mini kit (Qiagen; Valencia, Calif.). Viral RNA was reverse-transcribed using AccuScript High Fidelity Reverse Transcriptase (Stratagene Agilent; Santa Clara, Calif.) and 0.5 µM of the corresponding antisense external primer in a 20-µl reaction mixture containing 1 mM dNTPs, 10 mM DTT and 10 units of RNase inhibitor. Viral cDNA was then PCR amplified using a series of external and nested primers with defined cycling conditions. The HIV-1 envelope gene was amplified as a 2,302 nt fragment, that is, all the surface glycoprotein (gp120) and most of the transmembrane glycoprotein (gp41), missing only 321 nt of the gp41 cytoplasmic domain. External PCR reactions were carried out in a 50-µl mixture containing 0.2 mM dNTPs, 3 mM MgCl2 and 2.5 units of Pfu Turbo DNA Polymerase (Stratagene). Nested PCR reactions were carried out in a 50-µl mixture containing 0.2 mM dNTPs, 0.3 units of Pfu Turbo DNA Polymerase and 1.9 units of Taq Polymerase (Denville Scientific; Metuchen, N.J.). PCR products corresponding to the gp120/gp41-coding regions of HIV-1 were purified with the QIAquick PCR Purification kit (Qiagen) and the V3 region sequenced (population sequence) using AP Biotech DYEnamic ET Terminator cycle with Thermosequenase II (Davis Sequencing LCC, Davis, Calif.). Nucleotide sequences were analyzed using DNASTAR Lasergene Software Suite v.7.1.0 (Madison, Wis.).

TABLE 4

PCR amplification of envelope from gp120 up to Tat exon 2

| STEP | PRIMER FWD | PRIMER BWD |
|---|---|---|
| cDNA | None | EXT TAT REC CON BWD 13 (SEQ ID NO: 3) |
| External PCR | TAT REC CON FWD 3 (SEQ ID NO: 7) | TAT REC CON BWD 7 (SEQ ID NO: 14) |
| Nested PCR | IntF gp120.3 (SEQ ID NO: 12) | TAT REC CON BWD 4 (SEQ ID NO: 10) |

Expression of Patient-Derived HIV-1 env Genes

The HIV-1 gp120/gp41-coding region was introduced into a vector using an innovative yeast-based cloning technology with minor modifications. Briefly, PCR products spanning the gp120/gp41-coding region of HIV-1 were introduced via yeast homologous recombination into the pRECnfl-LEU-ΔEnv(gp120-tatex2)/URA3 vector containing a near-full length HIV-1 genome with the yeast uracil biosynthesis (URA3) gene replacing the gp120/gp41 HIV-1 coding sequence (FIG. 1A). This construction expresses all HIV-1 coding regions, that is, all genes corresponding to the HIV-1NL4-3 strain used as backbone in the vector plus the patient-derived env gene; however it is unable to produce infectious virus since it is missing the 5' long terminal repeat (LTR) region. Following yeast transformation, vector DNA was purified from the entire number of yeast colonies (typically 200 to >1,000 individual colonies but not less than 333 colonies to achieve the 0.3% sensitivity) and used to transform Electrocomp TOP10 bacteria (Invitrogen). Plasmid DNA from all the bacteria preparation—to guarantee the continuity of the viral population that may have existed in vivo—was purified from 10 ml of bacteria (QIAprep Spin Miniprep Kit, Qiagen) and stored at −80° C. until further use.

Cell-to-Cell Fusion Assay to Determine HIV-1 Co-Receptor Tropism

The ability of HIV-1 to use CCR5 and/or CXCR4 as co-receptors to enter the host cell was quantified using a modified version of the α-complementation assay for HIV-envelope glycoprotein-mediated fusion. Briefly, 2 µg of the HIV-expression vector, carrying the patient-derived env gene, and 2 µg of a vector expressing the α fragment of the β-galactosidase gene (pCMVα) were co-transfected into $7\times10^5$ HEK293T (donor) cells using Lipofectamine 2000 (Invitrogen). The target cells (U87.CD4.CCR5 or U87.CD4.CXCR4) were transfected with 4 µg of a vector expressing the omega fragment (pCMVω) of the β-galactosidase gene. Forty-eight hours post-transfection the donor and target cells were washed three times with 1×PBS, removed from the cell-culture plates using a 1× solution of PBS and 3 mM EDTA, counted and re-suspended in DMEM at a concentration of $2\times10^6$ cells per milliliter. Fifty microliters ($1\times10^5$) of donor and target cells were mixed and added together into 96-well plate and incubated for 4 hours at 37° C. in 5% $CO_2$ (FIG. 1B). Cell-to-cell fusion events were quantified by measuring luminescence related to β-galactosidase activity (relative light units, RLU) using Galacto-star system (Applied Biosystems, Bedford, Mass.) in a multi-well plate reader (Victor V multilabel reader, PerkinElmer, Waltham, Mass.). Controls were run in each test, including mock cell and transfections with plasmid DNA mixtures containing (i) 100%+0%, (ii) 1%+99%, (iii) 0.3%+99.7%, and (iv) 0%+100% of vectors expressing the env gene from the X4 HIV-1NL4-3 or the R5 HIV-1BaL strains, respectively. Technical cutoffs for the quantification of env-mediated cell fusion events were calculated as the mean plus two standard deviations (SD) of the β-galactosidase activity detected after HEK293T cells, transfected with 100% R5 HIV-1BaL or 100% X4 HIV-1NL4-3, were incubated in cell-to-cell fusion experiments with U87.CD4.CXCR4 or U87.CD4.CCR5.cells, respectively.

454 Pyrosequencing of the V3 Region of env

Ultra-deep sequencing analysis of the V3 region was performed as previously described. Briefly, a 232 nt fragment encompassing the V3 region was generated by nested PCR from the same external PCR product used to construct the env-expression vector described above. The nested PCR was carried out with Phusion High-Fidelity DNA Polymerase (New England Biolabs, Ipswich, Mass.) in a 50 l-reaction mixture containing 0.2 mM dNTPs, 2.5 mM MgCl2, and 0.2 µM of both the antisense and barcoded sense primers. PCR products were purified with the QIAquick PCR Purification kit (Qiagen) and quantified with Quant-iT PicoGreen dsDNA kit (Invitrogen). Pooled PCR products were clonally amplified on capture beads in water-oil-emulsion micro-reactors. A total of 500,000 HIV-1 env enriched-DNA beads were deposited in the wells of a 454 GS FLX instrument (454 Life Sciences/Roche, Branford, Conn.) and pyrosequenced in forward direction using 200 cycles in a ten-hour sequencing run. Following the sorting of reads by barcode into sample-derived datasets, the reads were mapped and aligned to the corresponding reference sequence (i.e., global V3 sequence for each sample) using Segminator II. Within this software reads spanning the V3 loop were extracted, truncated, translated, and assembled for genotyping.

Genotypic Prediction of HIV-1 Co-Receptor Tropism

HIV-1 co-receptor tropism was predicted from population and 454 V3 sequences using several bioinformatics tools. In the case of population sequences, nucleotide mixtures were considered when the second highest peak in the electropherogram was above 25%, and then these nucleotide mixtures were translated into all possible permutations. The algorithms used to infer HIV 1 tropism from V3 amino acid sequences were: (i) Geno2Pheno (25), with false positive rates (FPR, predicted frequency of classifying an R5 sequence as non-R5 virus) based on optimized cutoffs associated with the analysis of clinical data from MOTIVATE (2.5% and 5.75%), 3.5% FPR as previously described or the recommendation from the European Consensus Group on clinical management of HIV-1 tropism testing (10%) as described in the Geno2Pheno website, (ii) Web PSSM using the subtype B x4r5 matrix, and (iii) the 11/24/25 charge rule implemented within our analysis pipeline. Finally, using the 454-pyrosequencing data, plasma samples were classified as containing non-R5 viruses if at least 0.3%, corresponding to the analytical sensitivity of the phenotypic tests VERITROP and Enhanced Sensitivity Trofile Assay (ESTA), or 2% of the individual sequences were predicted to benon-R5.

Statistical Analyses

Descriptive results are expressed as median values and interquartile ranges. Pearson correlation coefficient was used to determine the strength of association between categorical variables. All differences with a P value of <0.05 were considered statistically significant. All statistical analyses were performed using GraphPad Prism v.5.01 (GraphPad Software, La Jolla, Calif.) unless otherwise specified.

Results

Characterization of the RT-PCR Amplification

A 2,302 nt fragment of the HIV-1 env gene, containing the entire surface glycoprotein (gp120) and most of the transmembrane glycoprotein (gp41), was RT-PCR amplified to be used in the cell-to-cell fusion assay (FIG. 1). Amplifying these large PCR products can be challenging, particularly using clinical specimens with low viral loads. Thus, sensitivity of the RT-PCR amplification step was tested by analyzing 106 plasma samples obtained from two different clinical sources (i.e., the ACTU, Cleveland, Ohio, USA and the Hospital Carlos III, Madrid, Spain). Blood samples from HIV-infected individuals with plasma viral loads ranging from <50 to 10,000 copies of viral RNA/ml were used to PCR amplify the env fragment. RT-PCR products of the correct size were consistently obtained (96%, 77/80) in plasma samples with ≥1,000 copies/ml of HIV RNA (Table 6).

TABLE 5

| Viral load (copies/ml) | % Positive samples by RT-PCR (No. of Positive samples/total No. of samples tested)* |
|---|---|
| <50[b] | 0 (0/11) |
| 50-1,000 | 27 (4/15) |
| 1,001-5,000 | 93 (26/28) |
| 5,001-10,000 | 93 (13/14) |
| >10,000 | 100 (38/38) |

[a]RT-PCR amplification of patient-derived env fragments was performed with plasma samples (n = 106) from HIV infected individuals with viral loads ranging from <50 to >10,000 copies of viral RNA/ml as described in Materials and Methods.
[b]The plasma viral loads of some of these samples may have been zero.

Highly reproducible success in RT-PCR amplification of the specified product was obtained when testing eighteen plasma samples with different viral loads. Finally, the specificity of the RT-PCR primers and reactions was analyzed using nucleic acids from a series of RNA and DNA viruses (i.e., HBV, HCV, HIV-2, HTLV-1, HTLV-2, BKV, EBV, HHV-6, HHV-7, CMV, HSV-1, HSV-2, and VZV). As expected, no cross-reactivity was observed with any of these viruses as all RT-PCR reactions failed to generate any detectable amplicons.

Cell-to-Cell Fusion Assay to Determine HIV-1 Co-Receptor Tropism: Proof-of-Concept Unlike previous approaches that utilize ligation-based cloning techniques or homologous recombination in mammalian cells to clone HIV-1 env genes, here we used a yeast-based recombination/gap repair method to introduce patient-derived HIV-1 env fragments into a vector with the final goal of determining HIV-1 tropism in a modified version of the α-complementation assay for HIV-envelope glycoprotein-mediated fusion. To test the system, mixtures of the env gene from 226 X4 HIV-1NL4-3 and R5 HIV-1BaL viruses (i.e., 100%+0%, 1%+99%, 0.3%+99.7%, and 0%+100%, respectively) were introduced into the HIV-expression vector and co-transfected with a vector expressing the α fragment of the β-galactosidase gene (pCMVα) into the HEK293T donor cells. The target cells (U87.CD4.CCR5 or U87.CD4.CXCR4) were transfected with a vector expressing the co fragment (pCMVω) of the β-galactosidase gene (FIG. 1). As shown in FIG. 2, and in each further experiment, cells transfected with vectors containing 100% NL4-3 or 100% BaL were used to calculate the cutoffs defining a query virus as CCR5- or CXCR4-tropic, respectively. Importantly, our assay was able to detect cells expressing X4 env genes at 0.3% of a population comprised mostly of R5-env expressing cells (FIG. 2). Finally, a series of controls ruled out the possibility of non-specific luminescence levels contributing to the quantification of X4 or R5 expression, e.g., false positives due to non-specific cell-to-cell fusion and/or α+ω fragments complementation events (FIG. 2).

Performance of the Novel HIV-1 Co-Receptor Tropism Assay

The success of any anti-HIV therapy based on a CCR5 antagonist depends on the ability of the HIV-1 tropism assay to detect minority non-R5 viruses within the HIV-1 population. For that reason, we evaluated extensively the analytical sensitivity of our novel HIV-1 tropism test to quantify non-R5 variants in mixtures of cells expressing R5 and X4 env genes. We first mixed plasmid DNA (R5 HIV-1BaL and X4 HIV-1NL4-3) at different proportions prior transfection of the HEK293T cells, which has been the standard approach used to determine the sensitivity of phenotypic HIV-1 tropism tests. As expected, our novel assay detected X4 env clones when they constituted 0.3% of the plasmid population and R5 env clones when present at 1% of the population (FIG. 3A). Next, we mixed yeast colonies prior plasmid DNA isolation (used to transfect HEK293T cells) and obtained similar results, i.e., 0.3% sensitivity detecting X4 expressing cells but we were able to also quantify R5 env clones present at 0.3% of the population (FIG. 3B). Finally, and more importantly, we mixed BaL and NL4-3 DNA prior to PCR amplification (one of the first steps of the assay, FIG. 1B) mimicking the presence of R5 and X4 cDNA after RT-PCR and again, detected 0.3% of cells expressing the X4 or R5 env genes in mixtures of cells mostly expressing R5 or X4 env genes, respectively (FIG. 3C).

Reproducibility of the novel HIV-1 tropism assay was first evaluated by testing DNA from three viruses with different and known HIV-1 co-receptor usage (X4 HIV-1NL4-3, R5 HIV-1BaL, and dual/mixed HIV-110-172), ten times (10× replicates), by three operators, with distinct lots of critical reagents over a 4-week period. VERITROP accurately and repeatedly identified the viruses as X4, R5, and dual-mixed (FIG. 4A). More importantly, good reproducibility of the entire assay (from RNA extraction to cell-to-cell fusion) was found when over a 14-day period, two different operators analyzed two separate aliquots of 15 plasma samples from HIV-infected individuals using different lots of critical reagents (FIG. 4B).

Finally, although VERITROP was originally developed using subtype B HIV-1 strains, predominant in North America and Europe, it was important to test the ability of the assay to work with more worldwide prevalent non-B HIV-1 variants. For that, the phenotypic HIV-1 tropism of 26 viruses was assayed, including three subtype A (HIV-1A-93RW024, HIV-1A-92UG031, and HIV-1A-92UG029), four subtype B (HIV-1B-92BR014, HIV-1B-92TH593, HIV-1B-92US727, and HIV-1B-92US076), four subtype C (HIV-1C-96USNG58, HIV-1C-93MW959, HIV-1C-98IN022, and HIV-1C-92BR025), five subtype D (HIV-1D-92UG021, HIV-1D-92UG024, HIV-1D-94UG114, HIV-1D-92UG038, and HIV-1D-93UG065), two subtype F (HIV-1F-93BR20 and HIV-1F-93BR29), two subtype G (HIV-1G-RU132 and HIV-1G-RU570), and six circulating recombinant forms (HIV-1AE-CMU02, HIV-1AE-CMU06, HIV-1AE-92TH021, HIV-1AE-93TH051, HIV-1AE-95TH001, and HIV-1BF-93BR029). A 100% concordance was observed between the HIV-1 tropism determined by VERITROP with the predetermined co-receptor tropism known for each one of these viruses (Table 7). Interestingly, although inconclusive results were obtained with HIV-1 group O viruses, HIV-2, and SIV, VERITROP was able to determine the tropism of an HIV-1 group N strain.

TABLE 6

| Virus ID | env subtype[a] | Predetermined tropism[b] | Tropism by VERITROP[c] |
|---|---|---|---|
| 93RW024 | A | D/M | D/M |
| 92UG031 | A | R5 | R5 |
| 92UG029 | A | X4 | X4 |
| 92BR014 | B | D/M | D/M |
| 92HT593 | B | D/M | D/M |
| 92US727 | B | R5 | R5 |
| 92US076 | B | D/M | D/M |
| 96USNG58 | C | R5 | R5 |
| 93MW959 | C | R5 | R5 |
| 98IN022 | C | R5 | R5 |
| 92BR025 | C | R5 | R5 |
| 92UG021 | D | X4 | X4 |
| 92UG024 | D | X4 | X4 |

| Virus ID | env subtype a | Predetermined tropism b | Tropism by VERITROP c |
|---|---|---|---|
| 94UG114 | D | R5 | R5 |
| 92UG038 | D | X4 | X4 |
| 93UG065 | D | X4 | X4 |
| 93BR029 | F | R5 | R5 |
| 93BR020 | F | D/M | D/M |
| RU570 | G | R5 | R5 |
| RU132 | G | R5 | R5 |
| CMU02 | AE | X4 | X4 |
| CMU06 | AE | X4 | X4 |
| 92TH021 | AE | R5 | R5 |
| 93TH051 | AE | D/M | D/M |

TABLE 6-continued

| | | | |
|---|---|---|---|
| 92TH001 | AE | R5 | R5 |
| 93BR019 | BF | X4 | X4 |

Comparison of HIV-1 Tropism Data Obtained with VERITROP to Other Phenotypic or Genotypic HIV-1 Tropism Assays As described above, several phenotypic and genotypic HIV-1 co-receptor tropism methods have been developed, with the ESTA version of the phenotypic Trofile assay and genotypic tests based on population sequencing being widely used in the clinical setting. Here, the co-receptor tropism of viruses obtained from 76 HIV-infected individuals, screened to be treated with a maraviroc-containing regimen, was analyzed using two phenotypic (VERITROP and Trofile) and two genotypic (population and 454 sequencing, together with a series of algorithms to infer HIV-1 tropism from V3 sequences) assays. Hierarchical clustering analysis grouped the different HIV-1 co-receptor tropism determinations based not only on the sequencing method (population vs. 454) but also on the algorithm (11/24/25, Geno2Pheno, or PSSM) and threshold used for the detection of individual non-R5 sequences within the population (0.3% vs. 2%) (FIG. 5A). HIV-1 tropism determinations based on 454 sequencing clustered together by algorithm, regardless of the threshold for the detection of individual non-R5 sequences, with the exception of the data obtained using Geno2Pheno 3.5% (65.8%) and 10% (68.4%) FPR with a 0.3% threshold that clustered with VERITROP (FIG. 5A). On the other hand, the original Trofile assay showed a better overall correlation (79.3%) with population sequencing using either Geno2Pheno or PSSM (FIG. 5A). Interestingly, a 73.7% (56/76) concordance was observed between the two phenotypic tests, VERITROP and Trofile, with 19 of the 20 discordant results corresponding to non-R5 variants detected by VERITROP and not by the original Trofile assay (FIG. 5A).

As described above, this cohort of 76 HIV-infected individuals was screened for the presence of CXCR4-tropic viruses using the original Trofile assay before entering a maraviroc-containing regimen. Non-R5 viruses were detected in 27 patients (who were not treated with maraviroc) while 9 failed to respond to the therapy (i.e., plasma viral load above 400 copies/ml at week 12), presumably due to the presence of undetected non-R5 viruses. Thus, the ability to predict the success of the maraviroc-based regimen by a given HIV-1 tropism test was calculated as the percentage of patients identified as carrying non-R5 viruses at baseline relative to the patients who were not able to enter (n=27) or failed to respond to the maraviroc-based treatment (n=9), i.e., 27/36 or 75% in the case of Trofile (FIG. 5B). Based on this calculation, HIV-1 tropism assays based on population sequencing showed the lowest prediction ability (44.4% to 58.3%) followed by the test based on 454 sequencing (55.6% to 86.1%), depending on the algorithm and threshold used (FIG. 5B). Interestingly, HIV-1 tropism analysis based on 454 sequencing using Geno2Pheno 10% FPR, 0.3% threshold (31/36, 86.1%) and the phenotypic test VERITROP (29/36, 80.6%) seem to have more accurately predicted the success of the maraviroc-based therapy (FIG. 5B).

Detection of Low-Level CXCR4

Figure 6A:
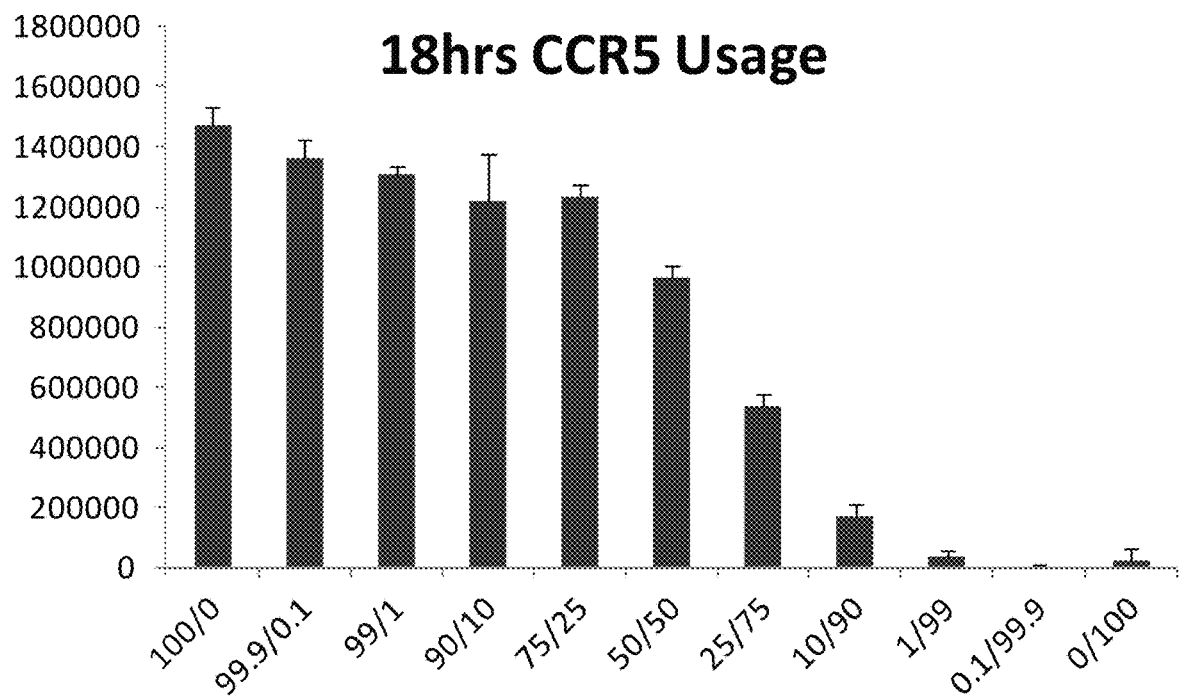
FIGS. 6(A-B) illustrate graphs showing VERITROP sensitively detects both (A) CXCR4 and (B) CCR5 using viruses after 18 hrs.
Figure 6B:
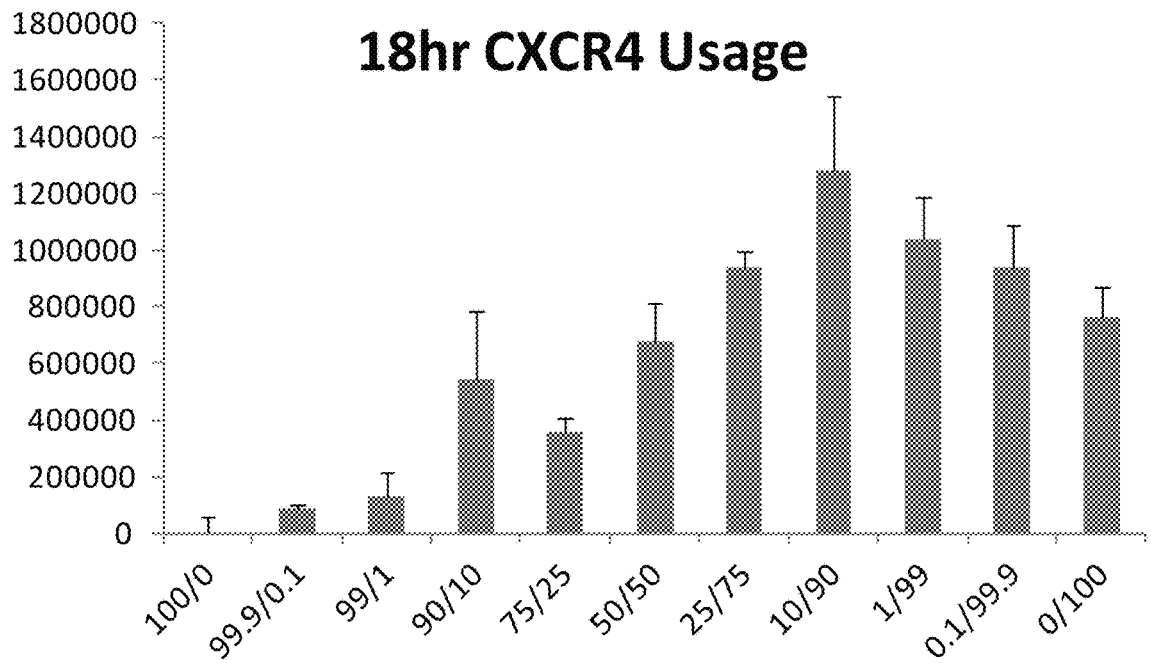

As shown in FIG. 6(A), VERITROP assay sensitivity detects CXCR4 and CCR5 using viruses after 18 hrs. pREC-nfl from an CXCR4 envelope was mixed with a pREC-nfl from an CCR5 envelope and then transfected 293T cells. We then mixed the transfected 293T cells with the U87.CD4 cells expressing either CCR5 or CXCR4.

Figure 7:
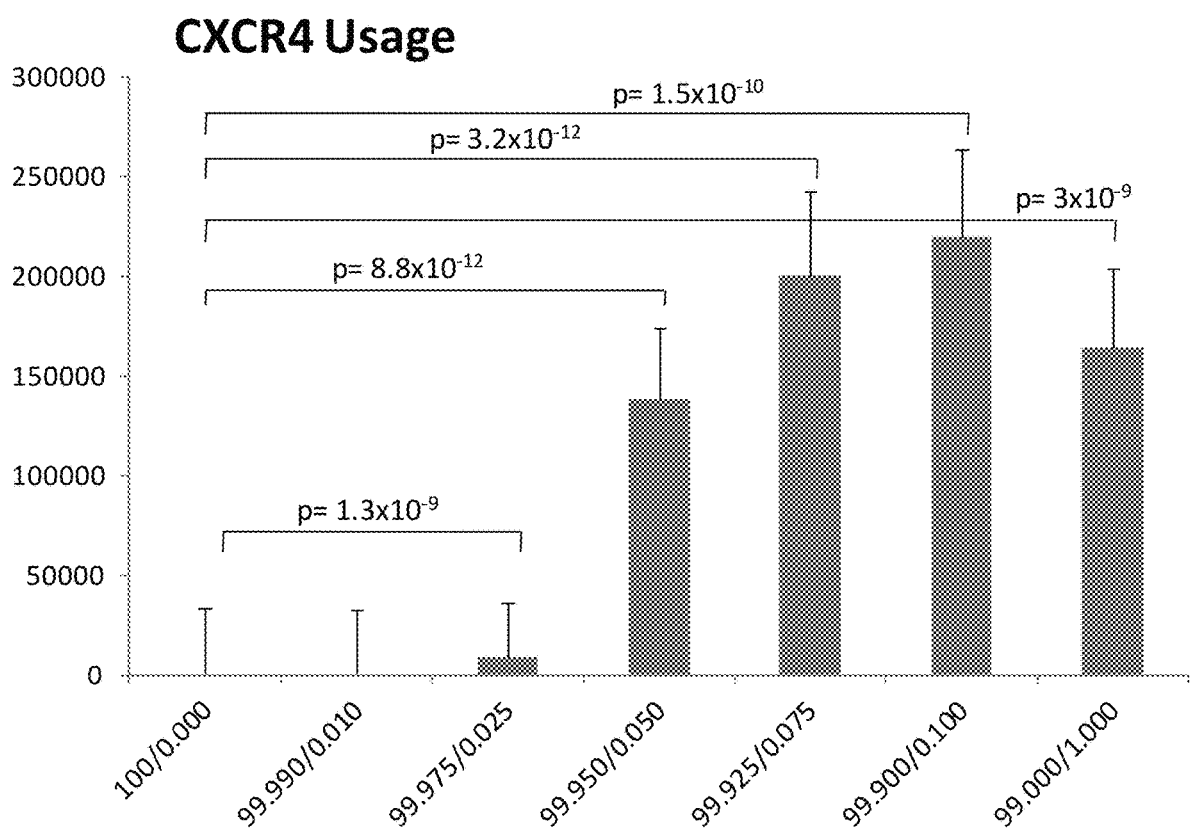
FIG. 7 illustrates a graph showing the high level of sensitivity in detecting CXCR4 using virus (1 out of every 2000 in a swarm). Each condition repeated 12×.

FIG. 7 shows a high level of sensitivity in detecting CXCR4 using virus (1 out of every 2000 in a swarm) where each condition is repeated 12×.

Figure 8:
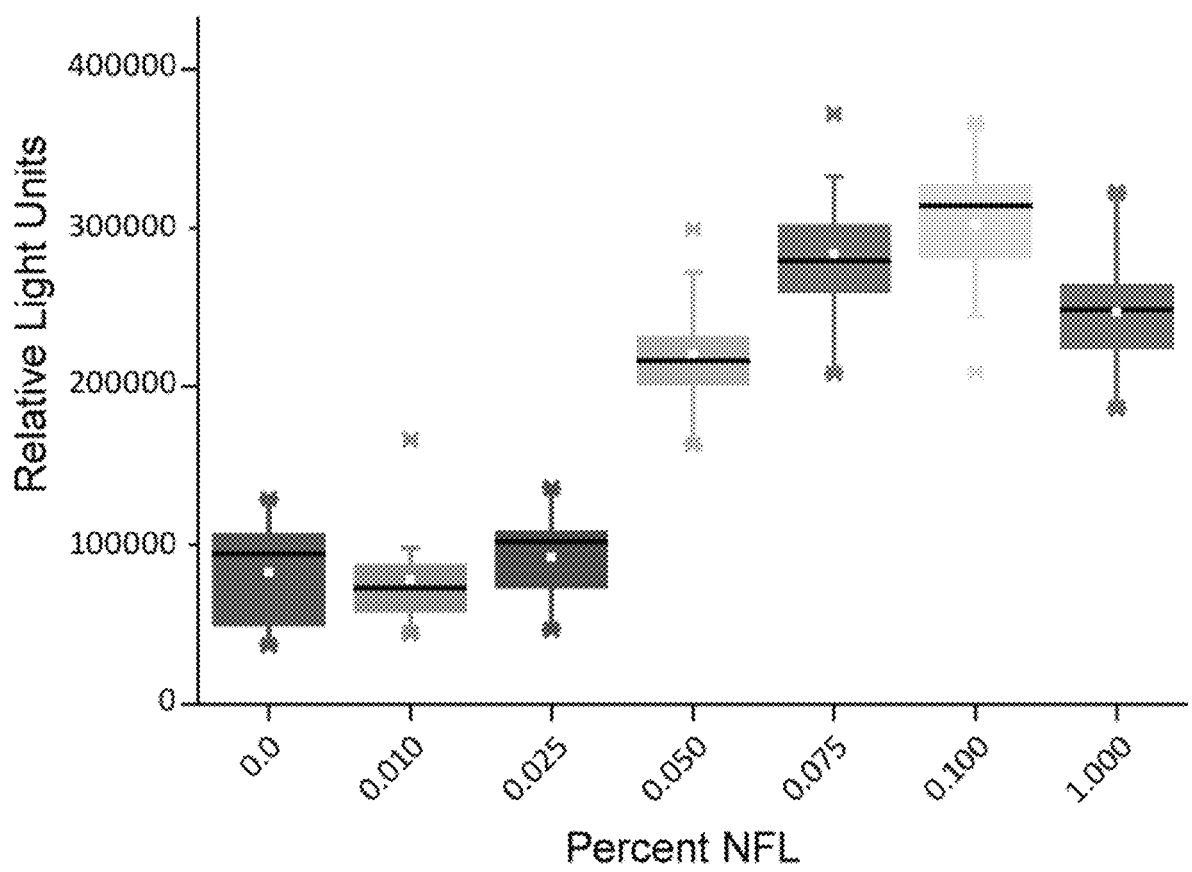
FIG. 8 illustrates a graph showing the analysis of samples having differing NFL percentages done in dodeclicate (12×) measured in relative light units (RLU).

As shown in FIG. 8, 12 samples were analyzed having differing NFL percentages. Analysis of 12 samples divided into individual triplicates reveals that the smallest values of 0.05, 0.075, and 0.01 are still significantly greater than the largest negative control values.

Figure 9A:
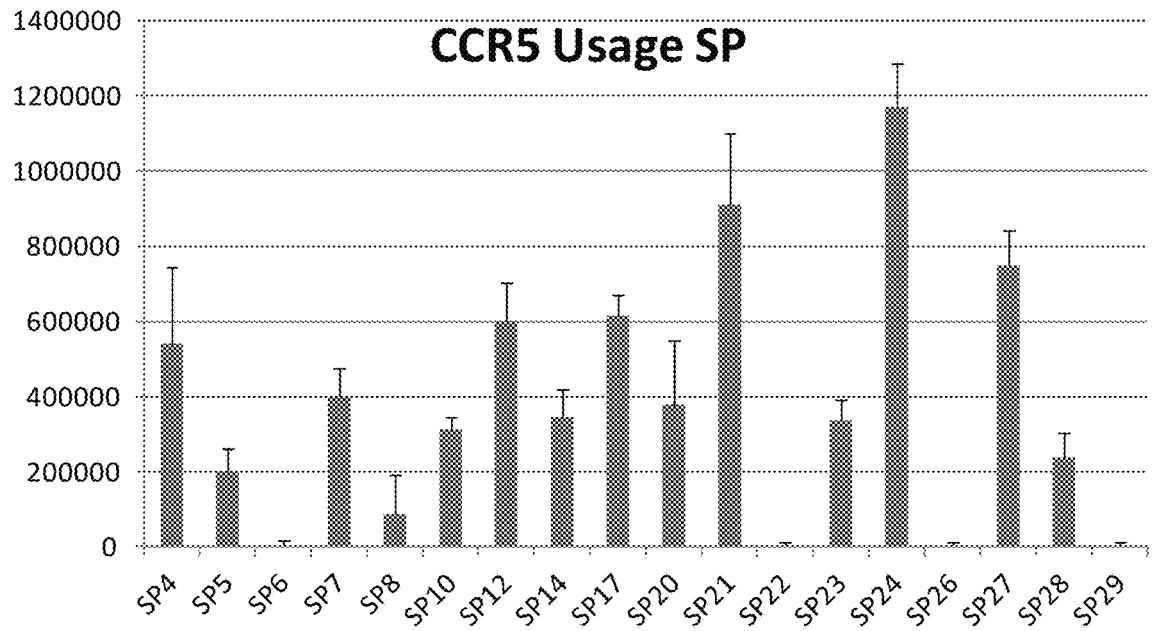
FIGS. 9(A-B) illustrate graphs showing tropism results in 18 patient derived viruses for (A) CCR5 versus (B) CXCR4 usage measured in relative light units (RLU).
Figure 9B:
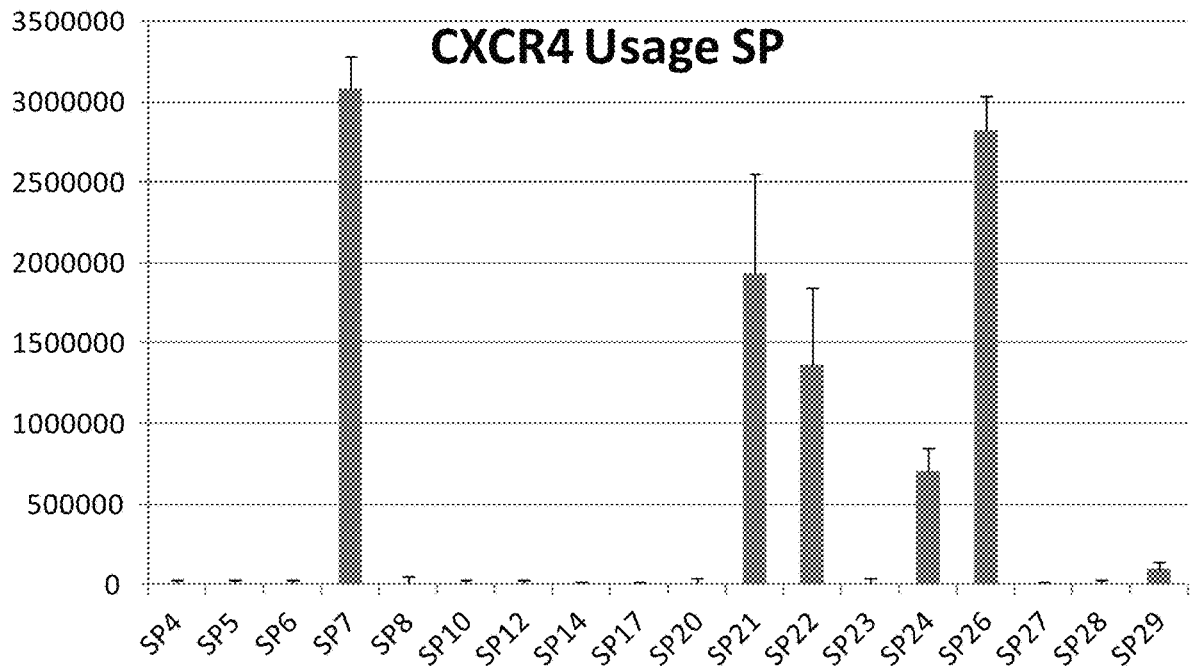
Figure 10A:
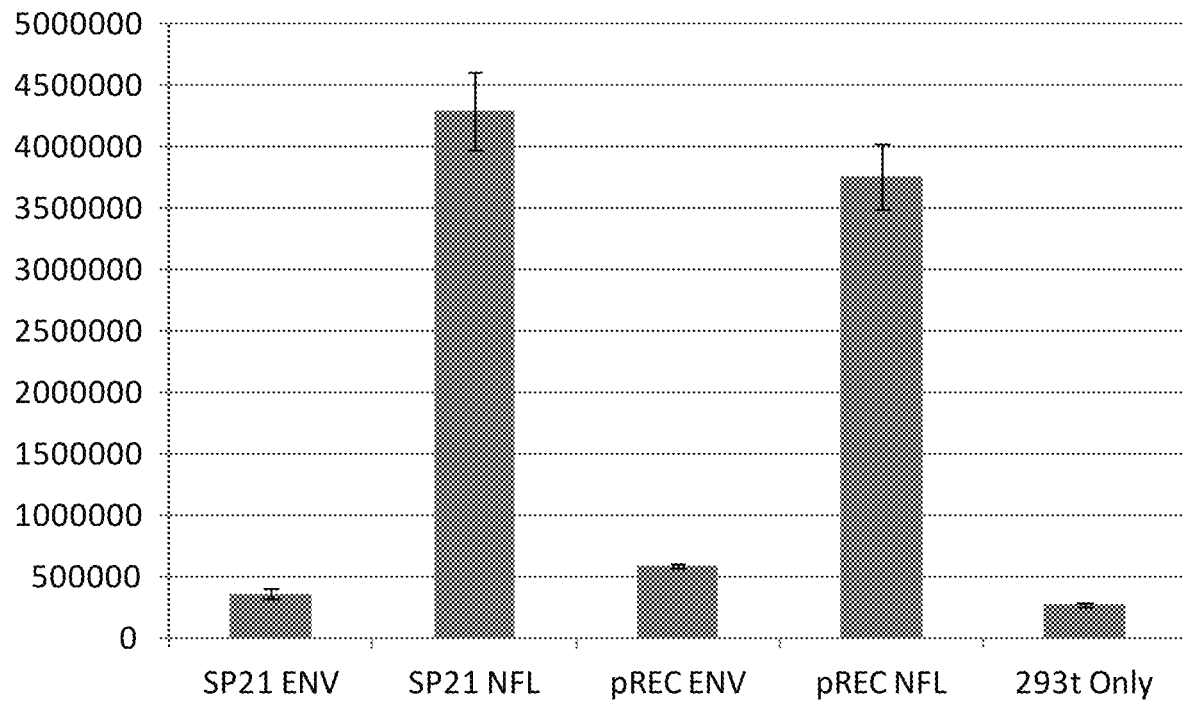
FIGS. 10A-B illustrate graphs showing that ENV only expression compared to NFL expression significantly reduced fusion efficiency.
Figure 10B:
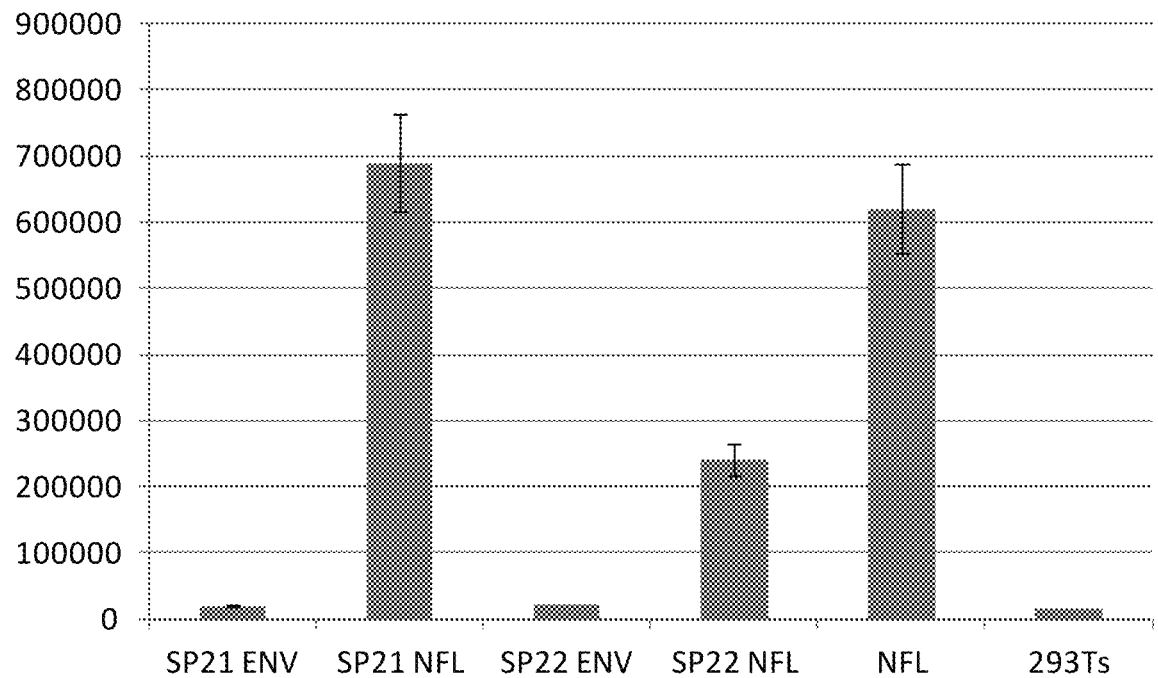

The system (VERITROP) involves cloning the patient-derived env gene into the pREC nfl vector. As shown in FIGS. 9-10, the VERITROP system results in much higher fusion efficiency compared to methods using both direct infectious virus addition and cell-to-cell fusion assays. FIG. 9(A-B) shows the results using a direct infectious virus addition system, i.e. cloning and producing a patient derived virus (SP #). We compared 18 patient derived viruses for CCR5 versus CXCR4 usage (FIGS. 9A and 9B respectively). We detected a new CXCR4 SP22 where the original tropism method missed SP22 dual-tropism. SP23 was too low to be determined. Our results matched or improved upon monograms results.

We know by western that ENV is expressed in pREC ENV clones. We observed reduced fusion efficiency between 293T cells expressing patient derived HIV-1 co-receptor protein and CXCR4 and CCR5 target cells using ENV expression vector compared to NFL. As shown in FIG. 10(A-B), patient derived ENV only expression used in cell-to-cell fusion assays where HIV-1 ENV from a patient is cloned into a vector and then transfected into a cell line to express HIV-1 Env glycoproteins significantly reduced fusion efficiency compared to the VERITROP system involving cloning the patient-derived env gene into the pREC nfl vector.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, we claim:

1. A method for determining HIV-1 co-receptor tropism in an HIV-infected patient, the method comprising:
    preparing an HIV-1 envelope protein coding sequence from a sample obtained from the patient, wherein the sample includes HIV-1 RNA, wherein the HIV-1 envelope protein coding sequence encodes HIV gp120 and an N-terminal portion of gp41 and does not encode a functional portion of the cytoplasmic domain of gp41, wherein the step of preparing an HIV-1 envelope protein coding sequence from a sample obtained from the patient comprises reverse transcribing the HIV-1 RNA to produce HIV-1 cDNA and amplifying a fragment of the HIV-1 cDNA by PCR amplification using external primers having SEQ ID NOs: 7 and 14 and nested primers having SEQ ID NOs: 10 and 12;
    introducing the HIV-1 envelope protein coding sequence into a first expression construct by providing a plasmid expression vector including a near-full length HIV-1 genome devoid of a 5' long terminal repeat and having a yeast uracil biosynthesis gene in place of a HIV-1 env coding sequence and replacing the yeast uracil biosynthesis gene with the HIV-1 envelope protein coding sequence prepared from the patient sample using yeast homologous recombination;
    transfecting a first cell with the first expression construct and a second expression construct, the second expression construct including a first reporter molecule fragment coding sequence, wherein the HIV-1 envelope protein and the first reporter molecule fragment are expressed on a cell surface of the first cell;
    providing a second cell that expresses a second reporter molecule fragment, a CD4 HIV-1 envelope protein receptor and CCR5 HIV-1 envelope protein co-receptor on a cell surface of the second cell, the second reporter molecule fragment capable of combining with first reporter molecule fragment to form a functional reporter molecule upon fusion of the first cell with the second cell;
    contacting the first cell with the second cell; and
    detecting the presence or absence of a signal produced by the functional reporter molecule, wherein the presence of a signal is indicative of CCR5 HIV-1 co-receptor tropism with the second cell.

2. The method of claim 1 further comprising the step of obtaining a blood plasma sample from the HIV-infected subject, the blood plasma sample comprising HIV-1 viral RNA.

3. The method of claim 1, wherein the step of introducing the HIV-1 envelope protein coding sequence into a first expression construct comprises providing a plasmid expression vector including a near-full length HIV-1 genome having a yeast uracil biosynthesis gene in place of a gp120/gp41 HIV-1 coding sequence and replacing the yeast uracil biosynthesis gene with the HIV-1 envelope protein coding sequence prepared from the patient sample.

4. The method of claim 1, wherein the second reporter molecule fragment is expressed by transfecting the second cell with a third expression construct, the third expression construct including a second reporter molecule fragment coding sequence encoding the second reported molecule.

5. The method of claim 1, wherein the presence of a signal compared to a control is indicative of CCR5 tropism in the HIV-infected patient.

6. The method of claim 1, the first cell comprising a HEK293T cell, and the second cell comprising a U97 cell stably expressing CD4 and an HIV-1 viral envelope protein co-receptor, wherein the HIV-1 viral envelope protein co-receptor is CCR5.

7. The method of claim 1, wherein the first reporter molecule fragment and the second reporter molecule fragment are different from each other and are independently selected from an α-fragment of β-galactosidase and an ω-fragment of β-galactosidase.

8. The method of claim 7, the first reporter molecule fragment comprising an α-fragment of β-galactosidase and the second reporter molecule fragment comprising an ω-fragment of β-galactosidase.

9. The method of claim 1, the first expression construct comprising a promoter operably linked to the HIV-1 envelope protein coding sequence from a sample prepared from the patient sample.

* * * * *